(12) United States Patent
Chen et al.

(10) Patent No.: US 8,460,653 B2
(45) Date of Patent: Jun. 11, 2013

(54) SUPEROXIDE DISMUTASE VARIANTS AND METHODS OF USE THEREOF

(75) Inventors: Danica Chen, San Francisco, CA (US); Xiaolei Qiu, San Ramon, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/237,733

(22) Filed: Sep. 20, 2011

(65) Prior Publication Data

US 2012/0121568 A1    May 17, 2012

Related U.S. Application Data

(60) Provisional application No. 61/452,812, filed on Mar. 15, 2011, provisional application No. 61/384,997, filed on Sep. 21, 2010.

(51) Int. Cl.
*A61K 38/44* (2006.01)
*A61K 38/00* (2006.01)
*C12N 9/02* (2006.01)

(52) U.S. Cl.
USPC .......................... 424/94.4; 435/189; 514/1.1

(58) Field of Classification Search
None
See application file for complete search history.

(56) References Cited

PUBLICATIONS

Purrello et al., "In Vitro and in Silico Cloning of Xenopus laevis SOD2 cDNA and Its Phylogenetic Analysis", DNA Cell Biol. 24:111-116, 2005.*
Chen et al., "Tumour suppressor SIRT3 deacetylates and activates manganese superoxide dismutase to scavenge ROS", EMBO reports 12:534-541, 2011.*
Qiu, Xiaolei, et al. "Calorie Restriction Reduces Oxidative Stress by SIRT3-Mediated SOD2 Activation", Cell Metabolism, Dec. 1, 2010, 12, pp. 662-667.

* cited by examiner

*Primary Examiner* — David J Steadman
(74) *Attorney, Agent, or Firm* — Paula A. Borden; Bozicevic, Field & Francis LLP.

(57) ABSTRACT

The present disclosure provides variant superoxide dismutase polypeptides, compositions comprising the polypeptides, and nucleic acids comprising nucleotide sequences encoding the polypeptides. The present disclosure provides methods of reducing oxidative damage in a cell, tissue, or organ. The present disclosure provides methods of identifying agents that increase superoxide dismutase activity.

11 Claims, 11 Drawing Sheets

```
Hs    1    M-LSR-AVCG--TSRQLAPVLGYLGSR-QKHSLPDLPYDYGALEPHINAQIMQLHHSKHHAAYVN
Mm    1    M-LCR-AACS--TGRRLGPVAGAAGSR-HKHSLPDLPYDYGALEPHINAQIMQLHHSKHHAAYVN
Dm    1    MFVAR-KISQ--TAS------LAVR-GKHTLPKLPYDYAALEPIICREIMELHHQKHHQTYVN
Sp    1    M-LRF-LSKN--SVAAIRNVSIARGVH-TKATLPPLPYAYNALEPALSETIMKLHHDKHHQTYVN
Xl    1    M-LCRLSVCG--RGRMRCVPALAYSFCKEKHTLPDLPYDYGALQPHISAEIMQLHHSKHHATYVN
Sc    1    M-FAK-TAAANLTKKGLSLLSTTARR-TKVTLPDLKWDFGALEPYISGQINELHYTKHHQTYVN
Rn    1    M-LCR-AACS--AGRRLGPAASTAGSR-HKHSLPDLPYDYGALEPHINAQIMQLHHSKHHATYVN

*
Hs   61    NLNVTEEKYQEA----LAK------GDVTAQIALQPALKFNGGGHINHSIFWTNLSPN--GGGEP--K-GELLEA
Mm   61    NLNATEEKYHEA----LAK------GDVTTQVALQPALKFNGGGHINHTIFWTNLSPK--GGGEP--K-GELLEA
Dm   54    NLNAAEEQLEEA----KSK------SDTTKLIQLAPALRFNGGGHINHTIFWQNLSPN--KT-QP--S-DDLKKA
Sp   61    NLNAAQEKLADP----NL-------DLEGEVALQAAIKFNGGGHINHSLFWKILAPQKEGGGKPVTS-GSLHKA
Xl   63    NLNITEEKYAEA----LAK------GDVTTQVSLQAALKFNGGGHINHTIFWTNLSPN--GGGEP--Q-GELLDA
Sc   63    GFNTAVDQFQELSDLLAKEPSPANARKMIAIQQNIKFHGGGFTNHCLFWENLAPESQGGGEP--PTGALAKA
Rn   61    NLNVTEEKYHEA----LAK------GDVTTQVALQPALKFNGGGHINHSIFWTNLSPK--GGGEP--K-GELLEA

Hs  121    IKRDFGSFDKFKEKLTAASVGVQGSGWGWLGFNKERG-HLQIAACPNQDPLQGTTGLIPLL
Mm  121    IKRDFGSFEKFKEKLTAVSVGVQGSGWGWLGFNKEQG-RLQIAACSNQDPLQGTTGLIPLL
Dm  113    IESQWKSLEEFKKELTTLTVAVQGSGWGWLGFNKKSG-KLQAALPNQDPLEASTGLIPLF
Sp  123    ITSKWGSLEDFQKEMNAALASIQGSGWAWLIVDKD-G-SLRITTANQDTIVKSK---PII
Xl  123    IKRDFGSFEKFKEKLNTVSVGVQGSGWGWLGYNKDSN-RLQLAACANQDPLQGTTGLIPLL
Sc  133    IDEQFGSLDELIKLTNTKLAGVQGSGWAFIVKNLSNGGKLDVVQTYNQDTVTGP--LVPLV
Rn  121    IKRDFGSFEKFKEKLTAVSVGVQGSGWGWLGFNKEQG-RLQIAACSNQDPLQGTTGLIPLL

Hs  181    GIDVWEHAYYLQYKNVRPDYLKAIWNVINWENVTERYMACKK    (SEQ ID NO:1)
Mm  181    GIDVWEHAYYLQYKNVRPDYLKAIWNVINWENVTERYTACKK    (SEQ ID NO:2)
Dm  173    GIDVWEHAYYLQYKNVRPSYVEAIWDIANWDDISCRFQEAKKLGC (SEQ ID NO:3)
Sp  179    GIDAWEHAYYPQYENRKAEYFKAIWNVINWKEAESRYS--NR    (SEQ ID NO:4)
Xl  183    GIDVWEHAYYLQYKNVRPDYLKAIWNVINWENVTERYQASKK    (SEQ ID NO:5)
Sc  192    AIDAWEHAYYLQYQNKKADYFKAIWNVVNWKEASRRFDAGKI    (SEQ ID NO:6)
Rn  181    GIDVWEHAYYLQYKNVRPDYLKAIWNVINWENVSQRYIVCKK    (SEQ ID NO:7)
```

FIG. 5

Variant SOD2 polypeptides

```
1)   1 mlsravcgts rqlapvlgyl gsrqkhslpd lpydygalep hinaqimqlh hsrhhaayvn
2)   1 mlsravcgts rqlapvlgyl gsrqkhslpd lpydygalep hinaqimqlh hsrhhaayvn
3)   1 mlsravcgts rqlapvlgyl gsrqkhslpd lpydygalep hinaqimqlh hsrhhaayvn
4)   1 mlsravcgts rqlapvlgyl gsrqkhslpd lpydygalep hinaqimqlh hsrhhaayvn
5)   1 mlsravcgts rqlapvlgyl gsrqkhslpd lpydygalep hinaqimqlh hsrhhaayvn
6)   1 mlsravcgts rqlapvlgyl gsrqkhslpd lpydygalep hinaqimqlh hsrhhaayvn
7)   1 mlsravcgts rqlapvlgyl gsrqkhslpd lpydygalep hinaqimqlh hsrhhaayvn
8)   1 mlsravcgts rqlapvlgyl gsrqkhslpd lpydygalep hinaqimqlh hsrhhaayvn 1)  61 nlnvteekyq ealakgdvta qialqpalrf nggghinhsi fwtnlspngg gepkgellea
2)  61 nlnateekyq ealakgdvta qialqpalrf nggghinhsi fwtnlspngg gepkgellea
3)  61 nlnvteekyq ealakgdvtt qialqpalrf nggghinhsi fwtnlspngg gepkgellea
4)  61 nlnvteekyq ealakgdvta qvalqpalrf nggghinhsi fwtnlspngg gepkgellea
5)  61 nlnvteekyq ealakgdvta qialqpalrf nggghinhti fwtnlspngg gepkgellea
6)  61 nlnvteekyq ealakgdvta qialqpalrf nggghinhsi fwtnlspngg gepkgellea
7)  61 nlnvteekyq ealakgdvta qialqpalrf nggghinhsi fwtnlspngg gepkgellea
8)  61 nlnvteekyq ealakgdvta qialqpalrf nggghinhsi fwtnlspngg gepkgellea
```

FIG. 6A

```
1) 121 ikrdfgsfdk fkekltaasv gvqgsgwgwl gfnkerghlq iaacpnqdpl qgttglipll
2) 121 ikrdfgsfdk fkekltaasv gvqgsgwgwl gfnkerghlq iaacpnqdpl qgttglipll
3) 121 ikrdfgsfdk fkekltaasv gvqgsgwgwl gfnkerghlq iaacpnqdpl qgttglipll
4) 121 ikrdfgsfdk fkekltaasv gvqgsgwgwl gfnkerghlq iaacpnqdpl qgttglipll
5) 121 ikrdfgsfdk fkekltaasv gvqgsgwgwl gfnkerghlq iaacpnqdpl qgttglipll
6) 121 ikrdfgsfek fkekltaasv gvqgsgwgwl gfnkerghlq iaacpnqdpl qgttglipll
7) 121 ikrdfgsfdk fkekltavsv gvqgsgwgwl gfnkerghlq iaacpnqdpl qgttglipll
8) 121 ikrdfgsfdk fkekltaasv gvqgsgwgwl gfnkeqgrlq iaacpnqdpl qgttglipll
```

```
1) 181 gidvwehayy lqyknvrpdy lkaiwnvinw envterymac kk (SEQ ID NO:8)
2) 181 gidvwehayy lqyknvrpdy lkaiwnvinw envterymac kk (SEQ ID NO:9)
3) 181 gidvwehayy lqyknvrpdy lkaiwnvinw envterymac kk (SEQ ID NO:10)
4) 181 gidvwehayy lqyknvrpdy lkaiwnvinw envterymac kk (SEQ ID NO:11)
5) 181 gidvwehayy lqyknvrpdy lkaiwnvinw envterymac kk (SEQ ID NO:12)
6) 181 gidvwehayy lqyknvrpdy lkaiwnvinw envterymac kk (SEQ ID NO:13)
7) 181 gidvwehayy lqyknvrpdy lkaiwnvinw envterymac kk (SEQ ID NO:14)
8) 181 gidvwehayy lqyknvrpdy lkaiwnvinw envterymac kk (SEQ ID NO:15)
```

FIG. 6B

*Homo sapiens* SIRT3
GenBank AAD40851

MAFWGWRAAA ALRLWGRVVE RVEAGGGVGP FQACGCRLVL GGRDDVSAGL RGSHGARGEP LDPARPLQRP PRPEVPRAFR RQPRAAAPSF
FFSSIKGGRR SISFSVGASS VVGSGGSSDK GKLSLQDVAE LIRARACQRV VVMVGAGIST PSGIPDFRSP GSGLYSNLQQ YDLPYPEAIF
ELPFFHNPK PFFTLAKELY PGNYKPNVTH YFLRLLHDKG LLLRLYTQNI DGLERVSGIP ASKLVEAHGT FASATCTVCQ RPFPGEDIRA
DVMADRVPRC PVCTGVVKPD IVFFGEPLPQ RFLLHVVDFP MADLLLLGT SLEVEPFASL TEAVRSSVPR LLINRDLVGP LAWHPRSRDV
AQLGDVVHGV ESLVELLGWT EEMRDLVQRE TGKLDGPDK (SEQ ID NO:28)

FIG. 7

*Homo sapiens* SIRT3
GenBank AF083108

```
   1 atggcgttct ggggttggcg cgccgcggca gccctccggc tgtgggccg  ggtagttgaa
  61 cgggtcgagg ccggggagg  cgtgggccct tttcaggcct gcggctgtcg gctggtgctt
 121 ggcggcaggg acgatgtgag tgcggggctg agaggcagcc atggggcccg cggtgagcgc
 181 ttggacccgg cgcgccccctt gcagagaggcct cccagaccccg aggtgccag  ggcattccgg
 241 aggcagccga gggcagcagc tcccagtttc ttcttttcga gtattaaagg tggaagaagg
 301 tccatatctt tttctgtggg tgcttcaagt gttgttggaa gtggaggcag cagtgacaag
 361 gggaagcttt ccctgcagga tgtagctgag ctgattcggg ccagagcctg cagtcgccg
 421 gtggtcatgg tgggggccgg catcagcaca cccagtggca ttccagactt cagatcgccg
 481 gggagtggcc tgtacagcca cctccagcaa tacgatctcc cgtacccga  ggccattttt
 541 gaactcccat tcttcttca  caacccccaag cccttttca  ctttggccaa ggagctgtac
 601 cctgaaaact acaagcccaa cgtcactcac tactttctcc ggctgcttca tgacaagggg
 661 ctgcttctgc ggctctacac gcagaacatc gatggcttg  agagagtgtc gggcatccct
 721 gcctcaaagc tggttgaacc tcatgaacc  tttgcctctg ccacctgcac agtctgccaa
 781 agacccttcc cagggagga  cattcgggct gacgtgatgg cagacagggt tccccgctgc
 841 ccggtctgca gggcgttgt  gaagcccgac attgtgttct ttggggagcc gctgccccag
 901 aggttcttgc tgcatgtggt tgatttcccc atggcagatc tgctgctcat cctttgggac
 961 tccctggagg tggagcctt  tgccagcttg accgaggccg ttgcttggc  atcctcgcga
1021 ctgctcatca accgggactt ggtggggccc tcacggcgtg gaaagcctag tggagcttct
1081 gcccagctgg gggacgtggt tcacggcgtg tcacggcgtg tggagcttct ggctggaca
1141 gaagagatgc gggacctttgt gcagcgggaa actgggaagc ttgatggacc agacaaatag
```

FIG. 8

(SEQ ID NO:29)

SUPEROXIDE DISMUTASE VARIANTS AND METHODS OF USE THEREOF

BACKGROUND

Superoxide radicals and other highly reactive oxygen species are harmful by-products produced in every respiring cell, causing oxidative damage to a wide variety of macromolecules and cellular components.

SUMMARY OF THE INVENTION

The present disclosure provides variant superoxide dismutase polypeptides, compositions comprising the polypeptides, and nucleic acids comprising nucleotide sequences encoding the polypeptides. The present disclosure provides methods of reducing oxidative stress and/or damage in a cell, tissue, or organ. The present disclosure provides methods of identifying agents that increase superoxide dismutase activity.

BRIEF DESCRIPTION OF THE DRAWINGS

FIG. 5 provides an alignment of amino acid sequences of SOD2 of various species.

FIGS. 6A and 6B provide amino acid sequences of exemplary SOD2 variants.

FIG. 7 provides an amino acid sequence of a human SIRT3 polypeptide.

FIG. 8 provides a nucleotide sequence encoding the human SIRT3 polypeptide depicted in FIG. 7.

DEFINITIONS

Figure 1:
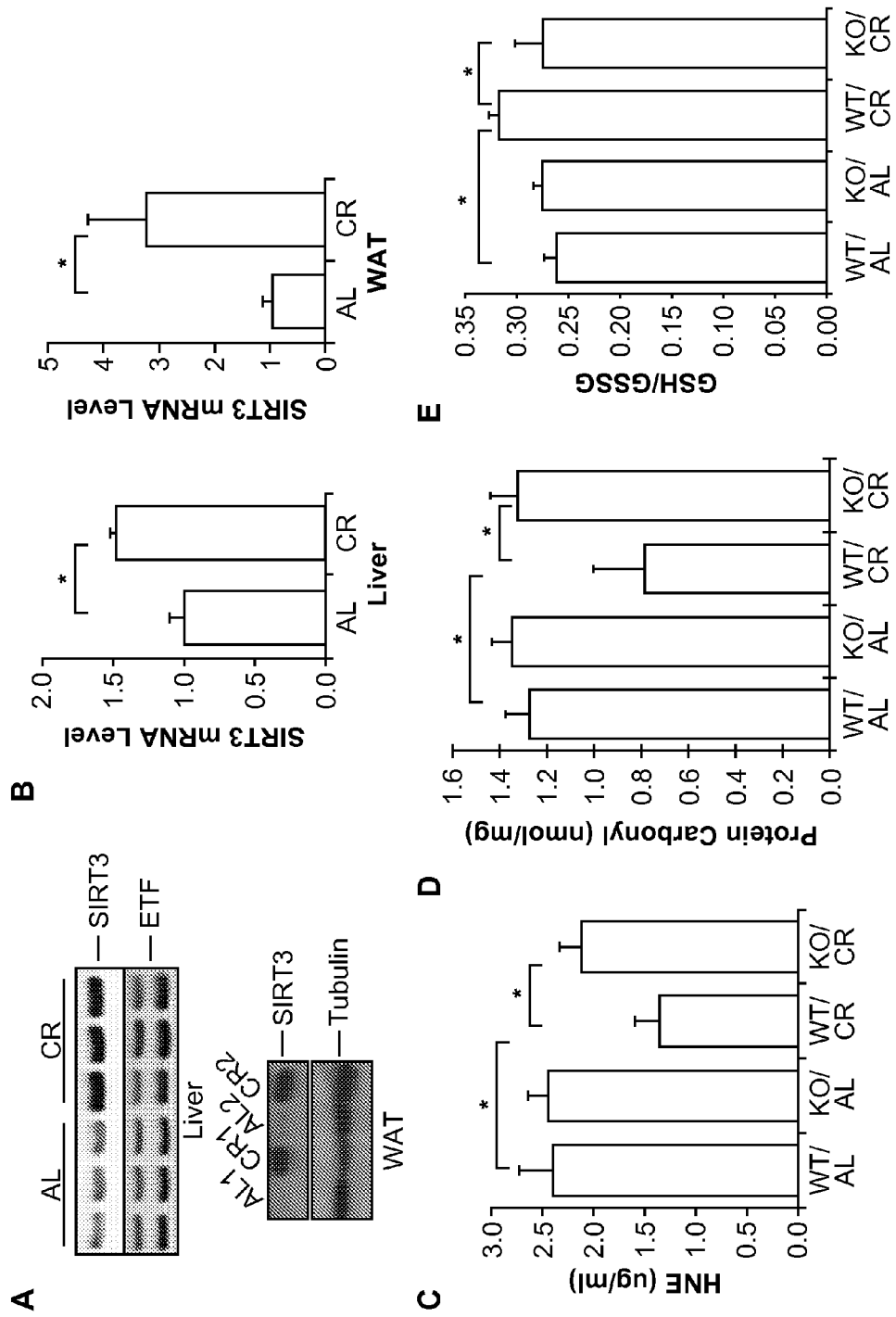
FIGS. 1A-E depict the requirement for SIRT3 in reduction of oxidative stress and damage by calorie restriction.

The terms "polypeptide," "peptide," and "protein," used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. $NH_2$ refers to the free amino group present at the amino terminus of a polypeptide. COOH refers to the free carboxyl group present at the carboxyl terminus of a polypeptide. In keeping with standard polypeptide nomenclature, *J. Biol. Chem.*, 243 (1969), 3552-59 is used.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The nucleic acid may be double stranded, single stranded, or contain portions of both double stranded or single stranded sequence. As will be appreciated by those in the art, the depiction of a single strand ("Watson") also defines the sequence of the other strand ("Crick"). By the term "recombinant nucleic acid" herein is meant nucleic acid, originally formed in vitro, in general, by the manipulation of nucleic acid by endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Nucleic acid sequence identity (as well as amino acid sequence identity) is calculated based on a reference sequence, which may be a subset of a larger sequence, such as a conserved motif, coding region, flanking region, etc. A reference sequence will usually be at least about 18 residues long, more usually at least about 30 residues long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17).

The term "genetic modification" and refers to a permanent or transient genetic change induced in a cell following introduction into the cell of new nucleic acid (i.e., nucleic acid exogenous to the cell). Genetic change ("modification") can be accomplished by incorporation of the new nucleic acid into the genome of the host cell, or by transient or stable maintenance of the new nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells. An isolated polypeptide will in some embodiments be synthetic. "Synthetic polypeptides" are assembled from amino acids, and are chemically synthesized in vitro, e.g., cell-free chemical synthesis, using procedures known to those skilled in the art.

By "purified" is meant a compound of interest (e.g., a polypeptide) has been separated from components that accompany it in nature. "Purified" can also be used to refer to a compound of interest separated from components that can accompany it during manufacture (e.g., in chemical synthesis). In some embodiments, a compound is substantially pure when it is at least 50% to 60%, by weight, free from organic molecules with which it is naturally associated or with which it is associated during manufacture. In some embodiments, the preparation is at least 75%, at least 90%, at least 95%, or at least 99%, by weight, of the compound of interest. A substantially pure polypeptide can be obtained, for example, by chemically synthesizing the polypeptide, or by a combination of purification and chemical modification. A substantially pure polypeptide can also be obtained by, for example, affinity chromatography. Purity can be measured by any appropriate method, e.g., chromatography, mass spectroscopy, high performance liquid chromatography analysis, etc.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. In some embodiments, the individual is a human. In some embodiments, the individual is a murine.

The terms "treatment," "treating," "treat," and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

A "therapeutically effective amount" or "efficacious amount" means the amount of an agent that, when administered to a mammal or other subject for treating a disease, is sufficient to effect such treatment for the disease. The "therapeutically effective amount" will vary depending on agent, the disease or condition and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a superoxide dismutase variant polypeptide" includes a plurality of such polypeptides and reference to "the formulation" includes reference to one or more formulations and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides variant superoxide dismutase polypeptides, compositions comprising the polypeptides, and nucleic acids comprising nucleotide sequences encoding the polypeptides. The present disclosure provides methods of reducing oxidative stress and/or damage in a cell, tissue, or organ.

Variant Superoxide Dismutase Polypeptides

The present disclosure provides variant superoxide dismutase polypeptides, and compositions comprising the polypeptides.

A subject variant SOD2 polypeptide exhibits enzymatic activity that is at least about 25%, at least about 50%, at least about 75%, at least about 2-fold, at least about 2.5-fold, at least about 3-fold, at least about 4-fold, at least about 5-fold, at least about 6-fold, at least about 7-fold, at least about 8-fold, at least about 9-fold, or at least about 10-fold, or more than 10-fold, higher than the enzymatic activity of a SOD2 polypeptide comprising the amino acid sequence set forth in SEQ ID NO:1 (*Homo sapiens* SOD2 amino acid sequence as depicted in FIG. 5).

Enzymatic activity of a subject variant SOD2 polypeptide can be determined using any known method, where a suitable method includes that described in Schisler and Singh (1985) *Biochem. Genet.* 23:291.

A subject variant SOD2 polypeptide comprises amino acid substitutions of at least K53 and K89, compared to the amino acid sequence set forth in SEQ ID NO:1. Thus, e.g., a subject variant SOD2 polypeptide can comprise an amino acid sequence having at least about 85%, at least about 90%, at least about 95%, at least about 98%, up to about 99%, amino acid sequence identity to the amino acid sequence set forth in SEQ ID NO:1, where the variant SOD2 polypeptide comprises amino acid substitutions at K53 and K89 compared with the amino acid sequence set forth in SEQ ID NO:1.

Amino acid sequences of exemplary SOD2 variants are depicted in FIGS. 6A and 6B. In some embodiments, a subject variant SOD2 polypeptide comprises an amino acid sequence having at least about 85%, at least about 90%, at least about 95%, at least about 98%, at least about 99%, or 100%, amino acid sequence identity to an amino acid sequence depicted in FIGS. 6A and 6B and set forth in SEQ ID NOs:8-15, where amino acids 53 and 89 are not lysine.

In some embodiments, a subject variant SOD2 polypeptide comprises one or more modifications such as: 1) a poly(ethylene glycol) (PEG) moiety; 2) a saccharide moiety; 3) a carbohydrate moiety; 4) a myristyl group; 5) a lipid moiety; and the like.

In some embodiments, a subject variant SOD2 polypeptide comprises a protein transduction domain. "Protein Transduction Domain" or PTD refers to a polypeptide, polynucleotide, carbohydrate, or organic or inorganic compound that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of a subject variant SOD2 polypeptide. In some embodiments, a PTD is covalently linked to the carboxyl terminus of a subject variant SOD2 polypeptide.

Exemplary protein transduction domains include but are not limited to a minimal undecapeptide protein transduction domain (corresponding to residues 47-57 of HIV-1 TAT comprising YGRKKRRQRRR; SEQ ID NO:16); a polyarginine sequence comprising a number of arginines sufficient to direct entry into a cell (e.g., 3, 4, 5, 6, 7, 8, 9, 10, or 10-50 arginines); a VP22 domain (Zender et al., Cancer Gene Ther. 2002 June; 9(6):489-96); an *Drosophila Antennapedia* protein transduction domain (Noguchi et al., Diabetes 2003; 52(7):1732-1737); a truncated human calcitonin peptide (Trehin et al. Pharm. Research, 21:1248-1256, 2004); polylysine (Wender et al., PNAS, Vol. 97:13003-13008); RRQRRTSKLMKR (SEQ ID NO:17); Transportan GWTLNSAGYLLGKINLKALAALAKKIL (SEQ ID NO:18); KALAWEAKLAKALAKALAKHLAKALAKALKCEA (SEQ ID NO:19); and RQIKIWFQNRRMKWKK (SEQ ID NO:20). Exemplary PTDs include but are not limited to, YGRKKRRQRRR (SEQ ID NO:16), RKKRRQRRR (SEQ ID NO:21); an arginine homopolymer of from 3 arginine residues to 50 arginine residues. Exemplary PTD domain amino acid sequences include, but are not limited to: YARAAARQARA (SEQ ID NO:22); THRLPRRRRRR (SEQ ID NO:23); and GGRRARRRRRR (SEQ ID NO:24).

In some embodiments, a subject SOD2 variant polypeptide comprises a peptide that facilitates entry into a mitochondrion. See, e.g., U.S. Pat. No. 7,470,661. In some embodiments, a subject SOD2 variant polypeptide comprises a peptide that facilitates entry into a neuronal cell (e.g., a neuron). See, e.g., U.S. Pat. No. 7,470,661. In some embodiments, a subject SOD2 variant polypeptide comprises a peptide that facilitates entry into a mitochondrion, and a peptide that facilitates entry into a neuronal cell. In some embodiments, the peptide that facilitates entry into a mitochondrion and/or the peptide that facilitates entry into a neuronal cell is linked to the variant SOD2 polypeptide by a protease-cleavable linker.

A subject SOD2 variant polypeptide will in some embodiments be linked to (e.g., covalently or non-covalently linked) a fusion partner, e.g., a ligand; an epitope tag; a peptide; a protein other than a subject SOD2 variant polypeptide; and the like. Suitable fusion partners include peptides and polypeptides that confer enhanced stability in vivo (e.g., enhanced serum half-life); provide ease of purification, e.g., $(His)_n$, e.g., 6His, and the like; provide for secretion of the fusion protein from a cell; provide an epitope tag, e.g., GST, hemagglutinin (HA; e.g., CYPYDVPDYA; SEQ ID NO:25), FLAG (e.g., DYKDDDDK; SEQ ID NO:26), c-myc (e.g., CEQKLISEEDL; SEQ ID NO:27), and the like; provide a detectable signal, e.g., an enzyme that generates a detectable product (e.g., β-galactosidase, luciferase), or a protein that is itself detectable, e.g., a green fluorescent protein, a red fluorescent protein, a yellow fluorescent protein, etc.; provides for multimerization, e.g., a multimerization domain such as an Fc portion of an immunoglobulin; and the like.

A subject variant SOD2 polypeptide can be made using any of a variety of established methods, e.g., conventional synthetic methods for protein synthesis; recombinant DNA methods; etc.

The present disclosure provides a composition comprising a subject variant SOD2 polypeptide. A subject variant SOD2 polypeptide composition can comprise, in addition to a subject variant SOD2 polypeptide, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

Nucleic Acids

The present disclosure provides a nucleic acid comprising a nucleotide sequence encoding a subject variant SOD2 polypeptide.

In some embodiments, a subject nucleic acid is an expression vector that, when introduced into a host cell, provides for production of a subject variant SOD2 polypeptide.

A nucleotide sequence encoding a subject variant SOD2 polypeptide can be operably linked to one or more regulatory elements, such as a promoter and enhancer, that allow expression of the nucleotide sequence in the intended target cells (e.g., a cell that is genetically modified to synthesize the encoded variant SOD2 polypeptide).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

Large numbers of suitable vectors and promoters are known to those of skill in the art; many are commercially available for generating a subject recombinant construct. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding a protein of interest. Suitable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus;

human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Cells

The present disclosure provides isolated genetically modified host cells (e.g., in vitro cells) that are genetically modified with a subject nucleic acid. In some embodiments, a subject isolated genetically modified host cell can produce a subject variant SOD2 polypeptide.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the host cell is *Escherichia coli*.

Compositions

The present disclosure provides compositions comprising a subject variant SOD2 polypeptide. In some embodiments, a subject composition comprises a subject variant SOD2 polypeptide and a pharmaceutically acceptable carrier. In some embodiments, a subject composition comprises a subject variant SOD2 polypeptide and at least one food-grade component.

A subject variant SOD2 polypeptide can be administered to a host using any convenient means capable of resulting in the desired therapeutic effect. Thus, a subject variant SOD2 polypeptide can be incorporated into a variety of formulations for therapeutic administration. More particularly, a subject variant SOD2 polypeptide can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, and injections.

In pharmaceutical dosage forms, a subject variant SOD2 polypeptide can be formulated alone or in appropriate association, as well as in combination, with other pharmaceutically active compounds. The following methods and excipients are merely exemplary and are in no way limiting.

For oral preparations, a subject variant SOD2 polypeptide can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject variant SOD2 polypeptide can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a subject variant SOD2 polypeptide are prepared by mixing the polypeptide having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-Methylglucosamine, galactosamine, and neuraminic acid; and/or non-ionic surfactants such as Tween, Brij Pluronics, Triton-X or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration; see also Chen (1992) Drug Dev Ind Pharm 18, 1311-54.

Exemplary variant SOD2 polypeptide concentrations in a subject pharmaceutical composition may range from about 1 mg/mL to about 200 mg/ml or from about 50 mg/mL to about 200 mg/mL, or from about 150 mg/mL to about 200 mg/mL.

An aqueous formulation of a subject SOD2 variant polypeptide may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the variant SOD2 polypeptide formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 nM.

A surfactant may also be added to the variant SOD2 polypeptide formulation to reduce aggregation of the formulated polypeptide and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Exemplary concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a subject variant SOD2 polypeptide, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

Furthermore, a subject variant SOD2 polypeptide can be made into suppositories by mixing with a variety of bases such as emulsifying bases or water-soluble bases. A subject variant SOD2 polypeptide can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise a subject variant SOD2 polypeptide in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a subject variant SOD2 polypeptide calculated in an amount sufficient to produce the desired effect in association with a pharmaceutically acceptable diluent, carrier or vehicle. The specifications for a subject variant SOD2 polypeptide may depend on the particular variant SOD2 polypeptide employed and the effect to be achieved, and the pharmacodynamics associated with each polypeptide in the host.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of a subject SOD2 variant polypeptide adequate to achieve the desired state in the subject being treated.

In some embodiments, a subject variant SOD2 polypeptide is formulated in a controlled release formulation. Sustained-release preparations may be prepared using methods well known in the art. Suitable examples of sustained-release preparations include semipermeable matrices of solid hydrophobic polymers containing a subject SOD2 variant polypeptide in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity may be prevented or reduced by using appropriate additives, by controlling moisture content and by developing specific polymer matrix compositions.

A subject composition can include a variant SOD2 polypeptide; and may also include known antioxidants, buffering agents, and other agents such as coloring agents, flavorings, vitamins or minerals. For example, a subject formulation may also contain one or more of the following minerals: calcium citrate (15-350 mg); potassium gluconate (5-150 mg); magnesium citrate (5-15 mg); and chromium picollinate (5-200 µg). In addition, a variety of salts may be utilized, including calcium citrate, potassium gluconate, magnesium citrate and chromium picollinate. Thickening agents may be added to the compositions such as polyvinylpyrrolidone, polyethylene glycol or carboxymethylcellulose. Exemplary additional components of a subject formulation include assorted colorings or flavorings, vitamins, fiber, milk, fruit juices, enzymes and other nutrients. Exemplary sources of fiber include any of a variety of sources of fiber including, but not limited to: psyllium, rice bran, oat bran, corn bran, wheat bran, fruit fiber and the like. Dietary or supplementary enzymes such as lactase, amylase, glucanase, catalase, and the like can also be included. Chemicals used in the present compositions can be obtained from a variety of commercial sources, including, e.g., Spectrum Quality Products, Inc (Gardena, Calif.), Sigma Chemicals (St. Louis, Mo.), Seltzer Chemicals, Inc., (Carlsbad, Calif.) and Jarchem Industries, Inc., (Newark, N.J.).

A subject formulation may also include a variety of carriers and/or binders. An exemplary carrier is micro-crystalline cellulose (MCC) added in an amount sufficient to complete dosage total weight. Carriers can be solid-based dry materials for formulations in tablet, capsule or powdered form, and can be liquid or gel-based materials for formulations in liquid or gel forms, which forms depend, in part, upon the routes of administration.

Exemplary carriers for dry formulations include, but are not limited to: trehalose, malto-dextrin, rice flour, micro-crystalline cellulose (MCC) magnesium sterate, inositol, fructo-oligosaccharide (FOS), gluco-oligosaccharide (GOS), dextrose, sucrose, and like carriers. Where the composition is dry and includes evaporated oils that produce a tendency for the composition to cake (adherence of the component spores, salts, powders and oils), dry fillers which distribute the components and prevent caking are included. Exemplary anti-caking agents include MCC, talc, diatomaceous earth, amorphous silica and the like, and are typically added in an amount of from approximately 1% to 95% by weight. It should also be noted that dry formulations which are subsequently rehydrated (e.g., liquid formula) or given in the dry state (e.g., chewable wafers, pellets, capsules, or tablets) can be used instead of initially hydrated formulations. Dry formulations (e.g., powders) may be added to supplement commercially available foods (e.g., liquid formulas, strained foods, or drinking water supplies). Similarly, the specific type of formulation depends upon the route of administration Suitable liquid or gel-based carriers include but are not limited to: water and physiological salt solutions; urea; alcohols and derivatives (e.g., methanol, ethanol, propanol, butanol); glycols (e.g., ethylene glycol, propylene glycol, and the like).

Generally, water-based carriers possess a neutral pH value (e.g., pH 7.0.+-.1.0 or 0.5 pH units). The compositions may also include natural or synthetic flavorings and food-quality coloring agents, all of which must be compatible with maintaining viability of the lactic acid-producing microorganism. Well-known thickening agents may also be added to the compositions such as corn starch, guar gum, xanthan gum, and the like.

A subject variant SOD2 polypeptide can be formulated to be suitable for oral administration in a variety of ways, for example in a liquid, a powdered food supplement, a paste, a gel, a solid food, a packaged food, a wafer, a tablet, a lozenge, a capsule, and the like. Other formulations will be readily apparent to one skilled in the art.

Although a subject variant SOD2 polypeptide may be directly ingested, or otherwise administered, or used as an additive in conjunction with foods, it will be appreciated that they may be incorporated into a variety of foods and beverages. The terms "food," "food product," and "foodstuff" are used interchangeably herein and include, in addition to foods commonly consumed by humans and domesticated animals, functional foods, pharmafoods, designer foods, and nutraceuticals. Suitable foods and beverages include, but are not limited to, yogurts, ice creams, cheeses, baked products such as bread, biscuits and cakes, dairy and dairy substitute foods, soy-based food products, grain-based food products, starch-based food products, confectionery products, edible oil compositions, spreads, breakfast cereals, infant formulas, juices, power drinks, and the like. Within the scope of the term "foods" are to be included in particular food likely to be classified as functional foods, i.e. "foods that are similar in appearance to conventional foods and are intended to be consumed as part of a normal diet, but have been modified to physiological roles beyond the provision of simple nutrient requirements" (NFA Policy Discussion Paper 7/94).

The present disclosure provides compositions (e.g., nutraceutical compositions) comprising a subject variant SOD2 polypeptide and a food-grade pharmaceutically acceptable excipient. In many embodiments, subject nutraceutical compositions include one or more components found in food products. Thus, the instant invention provides a food composition and products comprising an inactivated probiotic bacterium and a food component. Suitable components include, but are not limited to, mono- and disaccharides; carbohydrates; proteins; amino acids; fatty acids; lipids; stabilizers; preservatives; flavoring agents; coloring agents; sweeteners; antioxidants, chelators, and carriers; texturants; nutrients; pH adjusters; emulsifiers; stabilizers; milk base solids; edible fibers; and the like. The food component can be isolated from a natural source, or can be synthesized. All components are food-grade components fit for human consumption.

Methods of Reducing Oxidative Stress and/or Damage

The present disclosure provides methods of reducing oxidative stress and/or damage to a cell, tissue, or organ. In some embodiments, the methods involve contacting a cell, tissue, or organ (in vitro, in vivo, or ex vivo) with an effective amount of a subject variant SOD2 polypeptide. In some embodiments, the methods involve contacting a cell, tissue, or organ (in vitro, in vivo, or ex vivo) with combined effective amounts of a subject variant SOD2 polypeptide and a SIRT3 polypeptide. In some embodiments, the methods involve contacting a cell, tissue, or organ (in vitro, in vivo, or ex vivo) with combined effective amounts of a SOD2 polypeptide and a SIRT3 polypeptide. In some embodiments, the methods involve contacting a cell, tissue, or organ (in vitro, in vivo, or ex vivo) with combined effective amounts of a subject variant SOD2 polypeptide and an agent that increases enzymatic activity of SIRT3. In some embodiments, the methods involve contacting a cell, tissue, or organ (in vitro, in vivo, or ex vivo) with combined effective amounts of a subject variant SOD2 polypeptide and an agent that increases the level of a SIRT3 polypeptide, where an agent that increases the level of a SIRT3 polypeptide includes, e.g., a nucleic acid comprising a nucleotide sequence encoding a SIRT3 polypeptide.

Variant SOD2 Polypeptides

In some embodiments, a subject method of reducing oxidative stress and/or damage to a cell, tissue, or organ involves contacting the cell, tissue, or organ with an effective amount of a subject variant SOD2 polypeptide. The variant SOD2 polypeptide will in some instances enter a cell, and reduce oxidative damage to the cell and/or oxidative stress in the cell. A variant SOD2 can be administered to an individual in need thereof to reduce oxidative damage to a cell, tissue, or organ in the individual and/or reduce oxidative stress in a cell, tissue, or organ in the individual. Thus, the present disclosure provides methods of reducing oxidative damage and/or stress to a cell, tissue, or organ in an individual, the methods generally involving administering to the individual an effective amount of a subject variant SOD2 polypeptide. In some embodiments, a subject method comprises administering to an individual in need thereof combined effective amounts of a subject variant SOD2 polypeptide and a SIRT3 polypeptide.

An effective amount of a subject variant SOD2 polypeptide is an amount that reduces the level of ROS in a cell, tissue, or organ by at least about 10%, at least about 20%, at least about 25%, at least about 30%, at least about 40%, at least about 50%, at least about 60%, at least about 70%, at least about 80%, or more than 80%, compared to the level of ROS in the cell, tissue, or organ in the absence of a subject variant SOD2 polypeptide.

The oxidative damage is caused by free radicals, such as reactive oxygen species (ROS) and/or reactive nitrogen species (RNS). Examples of ROS and RNS include hydroxyl radical (HO.), superoxide anion radical ($O_2^-$), nitric oxide (NO.), hydrogen peroxide ($H_2O_2$), hypochlorous acid (HOCl), and peroxynitrite anion. ($ONOO^-$).

An individual in need of a subject treatment method includes an individual undergoing a treatment associated with oxidative damage and/or stress. For example, the individual may be undergoing reperfusion. Reperfusion refers to the restoration of blood flow to any organ or tissue in which the flow of blood is decreased or blocked. The restoration of blood flow during reperfusion leads to respiratory burst and formation of free radicals. Decreased or blocked blood flow can be due to hypoxia or ischemia. The loss or severe reduction in blood supply during hypoxia or ischemia can be due to thromboembolic stroke, coronary atherosclerosis, or peripheral vascular disease.

Numerous organs and tissues are subject to ischemia or hypoxia. Examples of such organs include brain, heart, kidney, intestine, and prostate. The tissue affected can be muscle, such as cardiac, skeletal, or smooth muscle. For instance, cardiac muscle ischemia or hypoxia is commonly caused by atherosclerotic or thrombotic blockages which lead to the reduction or loss of oxygen delivery to the cardiac tissues by the cardiac arterial and capillary blood supply. Such cardiac ischemia or hypoxia may cause pain and necrosis of the affected cardiac muscle, and ultimately may lead to cardiac failure. Ischemia or hypoxia in skeletal muscle or smooth muscle may arise from similar causes. For example, ischemia or hypoxia in intestinal smooth muscle or skeletal muscle of the limbs may also be caused by atherosclerotic or thrombotic blockages.

The restoration of blood flow (reperfusion) can occur by any method known to those in the art. For instance, reperfusion of ischemic cardiac tissues may arise from angioplasty, coronary artery bypass graft, or the use of thrombolytic drugs. Reducing oxidative damage associated with ischemia/hypoxia and reperfusion is important because the tissue damage associated with ischemia/hypoxia and reperfusion is associated with, for example, myocardial infarction, stroke, and hemorrhagic shock.

Individuals in need of treatment with a subject method include individuals with a disease or condition associated with oxidative damage and/or oxidative stress. The oxidative damage and/or oxidative stress can occur in any cell, tissue, or organ of the mammal. Examples of such cells, tissues, and organs include, but are not limited to, endothelial cells, epithelial cells, nervous system cells, skin, heart, lung, kidney, and liver. For example, lipid peroxidation and an inflammatory process are associated with oxidative damage.

A subject method is useful for reducing oxidative damage and/or oxidative stress associated with various neurodegenerative diseases and conditions. The neurodegenerative disease can affect any cell, tissue, or organ of the central or peripheral nervous system. Examples of such cells, tissues, and organs include the brain, spinal cord, neurons, ganglia, Schwann cells, astrocytes, oligodendrocytes, and microglia.

The neurodegenerative condition can be an acute condition, such as a stroke or a traumatic brain or spinal cord injury. In another embodiment, the neurodegenerative disease or condition is a chronic neurodegenerative condition. Examples of chronic neurodegenerative diseases associated with damage by free radicals include Parkinson's disease, Alzheimer's disease, Huntington's disease and amyotrophic lateral sclerosis.

Other conditions suitable for treatment with a subject method include preeclampsia; diabetes; and symptoms of and conditions associated with aging, such as age-related macular degeneration, and wrinkles.

A subject method is useful for reducing oxidative damage and/or oxidative stress in an organ of a mammal prior to transplantation. For example, a donor organ, when subjected to reperfusion after transplantation can be susceptible to oxidative damage. A subject variant SOD2 polypeptide can be used to reduce oxidative damage from reperfusion of the transplanted organ.

The donor organ can be any organ suitable for transplantation. Examples of such organs include, e.g., heart, liver, kidney, lung, and pancreatic islets. A donor organ is placed in a suitable medium ex vivo, where suitable media include a standard buffered solution commonly used in the art.

The present disclosure provides a method for reducing oxidative damage and/or oxidative stress in a cell. Cells include those cells in which the cell membrane or DNA of the cell has been damaged, or is at risk of damage, by free radicals, for example, ROS and/or RNS. Examples of cells suitable for treatment using a subject method include, but are not limited to, skin cells, pancreatic islet cells, myocytes, endothelial cells, neuronal cells, and stem cells. The cells can be in vitro or in vivo.

In some embodiments, the cells are in vitro. For example, the cells can be tissue culture cells. Alternatively, the cells can be obtained from a mammal. In one instance, the cells are those that have been damaged by oxidative damage and/or stress as a result of an insult. Such insults include, for example, a disease or condition (e.g., diabetes, etc) or ultraviolet radiation (e.g., sun, etc.). For example pancreatic islet cells damaged by oxidative damage and/or stress as a result of diabetes can be obtained from a mammal.

Where a subject method involves administering an effective amount of a subject variant SOD2 polypeptide to an individual, the variant SOD2 polypeptide is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, intraarterial, rectal, nasal, oral, and other enteral and parenteral routes of administration. Routes of administration may be combined, if desired, or adjusted depending upon the variant SOD2 polypeptide and/or the desired effect. A subject variant SOD2 polypeptide composition can be administered in a single dose or in multiple doses. In some embodiments, a subject variant SOD2 polypeptide composition is administered orally. In some embodiments, a subject variant SOD2 polypeptide composition is administered topically to the skin.

In some embodiments, a subject variant SOD2 polypeptide composition is administered locally. In some embodiments, a subject variant SOD2 polypeptide composition is administered systemically.

Variant SOD2 Polypeptide and SIRT3

As noted above, in some embodiments, a subject method comprises administering to an individual in need thereof combined effective amounts of a subject variant SOD2 polypeptide and a SIRT3 polypeptide. The SIRT3 polypeptide can be administered as a polypeptide per se, or as a nucleic acid comprising a nucleotide sequence encoding a SIRT3 polypeptide. The nucleic acid comprising a nucleotide sequence encoding a SIRT3 polypeptide can be a recombinant expression vector. Exemplary suitable expression constructs are described above. A SIRT3 polypeptide can comprise an amino acid sequence having at least about 85%, at least about 90%, at least about 95%, at least about 98%, at least about 99%, or 100%, amino acid sequence identity to a contiguous stretch of from about 350 amino acids to about 399 amino acids of the amino acid sequence depicted in FIG. 7 and set forth in SEQ ID NO:28. A suitable SIRT3 nucleic acid can comprise a nucleotide sequence having at least about 85%, at least about 90%, at least about 95%, at least about 98%, at least about 99%, or 100%, nucleotide sequence identity to the nucleotide sequence depicted in FIG. 8 and set forth in SEQ ID NO:29. Suitable dosages, formulations, and routes of administration are as described above.

SOD2 and SIRT3

As noted above, in some embodiments, a subject method comprises administering to an individual in need thereof combined effective amounts of a SOD2 polypeptide and a SIRT3 polypeptide (or a nucleic acid comprising a nucleotide sequence encoding a SIRT3 polypeptide). A suitable SOD2 polypeptide comprises an amino acid sequence having at least about 85%, at least about 90%, at least about 95%, at least about 98%, at least about 99%, or 100%, amino acid sequence identity to the amino acid sequence set forth in SEQ ID NO:1. Suitable SIRT3 polypeptides, and suitable SIRT3 nucleic acids, are as described above. Suitable dosages, formulations, and routes of administration are as described above.

SOD2 Polypeptide and Agent that Increases SIRT3 Enzymatic Activity

In some embodiments, a subject method of reducing oxidative stress and/or damage to a cell, tissue, or organ involves contacting the cell, tissue, or organ with combined effective amounts of: a) an SOD2 polypeptide, which may be a subject variant SOD2 polypeptide; and b) an agent that increases enzymatic activity of a SIRT3 polypeptide. The combination therapy can be administered to an individual in need thereof to reduce oxidative damage to a cell, tissue, or organ in the individual and/or reduce oxidative stress in a cell, tissue, or organ in the individual. Thus, the present disclosure provides methods of reducing oxidative damage and/or stress to a cell, tissue, or organ in an individual, the methods generally involving administering to the individual combined effective amounts of a SOD2 polypeptide (which can be a subject variant SOD2 polypeptide) and an agent that increases enzymatic activity of a SIRT3 polypeptide.

Agents that increase enzymatic activity of a SIRT3 polypeptide include small molecule agents (e.g., agents having a molecular weight in a range of greater than 25 daltons and less than about 10,000 daltons, e.g., a candidate agent may have a molecular weight of from about 25 daltons to about 50 daltons, from about 50 daltons to about 100 daltons, from about 100 daltons to about 150 daltons, from about 150 daltons to about 200 daltons, from about 200 daltons to about 500 daltons, from about 500 daltons to about 1000 daltons, from about 1,000 daltons to about 2500 daltons, from about 2500 daltons to about 5000 daltons, from about 5000 daltons to about 7500 daltons, or from about 7500 daltons to about 10,000 daltons.

Agents that increase enzymatic activity of a SIRT3 polypeptide include agents that increase enzymatic activity of a SIRT3 polypeptide by at least about 10%, at least about 25%, at least about 50%, at least about 2-fold, at least about 2.5-fold, at least about 5-fold, at least about 10-fold, at least about 25-fold, or more than 25-fold.

Agents that increase enzymatic activity of a SIRT3 polypeptide include, e.g., an agent as described in U.S. Patent Publication No. 2011/0046110; U.S. Patent Publication No. 2011/0039847; U.S. Patent Publication No. 2011/0015192; U.S. Pat. No. 7,893,086; U.S. Pat. No. 7,855,289; U.S. Pat. No. 7,829,556; U.S. Pat. No. 7,345,178. In some embodiments, an agent that increases SIRT3 enzymatic activity is selective for SIRT3, e.g., the agent does not substantially have one or more of the following activities: inhibition of PI3-kinase, inhibition of aldoreductase, inhibition of tyrosine kinase, transactivation of EGFR tyrosine kinase, coronary dilation, or spasmolytic activity, at concentrations of the compound that are effective for increasing the deacetylation activity of SIRT3. In some instances, an agent that increases SIRT3 activity may also increase enzymatic SIRT1 activity. In other instances, an agent that increases SIRT3 enzymatic activity does not substantially increase SIRT1 enzymatic activity. Assays for determining whether an agent increases SIRT3 activity are known in the art; a suitable assay is described in U.S. Pat. No. 7,893,086.

A suitable agent that increases SIRT3 activity can increase SIRT3 enzymatic activity with an $EC_{50}$ of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

Screening Methods

The present disclosure also provides methods of identifying agents that increase the enzymatic activity of a SOD2 polypeptide. The methods generally involve contacting a SOD2 polypeptide with a test agent in the presence of a substrate for SOD2; and determining the effect, if any, of the test agent on the enzymatic activity of the SOD2 polypeptide. The method can be carried out in vitro in a cell-free assay system, or can be carried out in vitro in a cell-based assay system. Thus, the present disclosure provides an in vitro cell-free method for identifying an agent that increases the enzymatic activity of a SOD2 polypeptide; and an in vitro cell-based method for identifying an agent that increases the enzymatic activity of a SOD2 polypeptide.

As used herein, the term "determining" refers to both quantitative and qualitative determinations and as such, the term "determining" is used interchangeably herein with "assaying," "measuring," and the like.

The terms "candidate agent," "test agent," "agent," "substance," and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 10,000 daltons, e.g., a candidate agent may have a molecular weight of from about 50 daltons to about 100 daltons, from about 100 daltons to about 150 daltons, from about 150 daltons to about 200 daltons, from about 200 daltons to about 500 daltons, from about 500 daltons to about 1000 daltons, from about 1,000 daltons to about 2500 daltons, from about 2500 daltons to about 5000 daltons, from about 5000 daltons to about 7500 daltons, or from about 7500 daltons to about 10,000 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a sample (e.g., a sample comprising the SOD2 polypeptide and the SOD2 substrate in the absence of the test agent). Generally a plurality of assay mixtures is run in parallel with different agent concentrations to obtain a differential response to the various concentrations. Typically, one of these concentrations serves as a negative control, i.e. at zero concentration or below the level of detection.

A variety of other reagents may be included in the screening assay. These include reagents like salts, neutral proteins, e.g. albumin, detergents, etc., including agents that are used to facilitate optimal enzyme activity and/or reduce non-specific or background activity. Reagents that improve the efficiency of the assay, such as protease inhibitors, anti-microbial agents, etc. may be used. The components of the assay mixture are added in any order that provides for the requisite activity. Incubations are performed at any suitable temperature, typically between 4° C. and 40° C. Incubation periods are selected for optimum activity, but may also be optimized to facilitate rapid high-throughput screening. Typically between 0.1 hour and 1 hour will be sufficient.

A test agent that increases enzymatic activity of the SOD2 polypeptide is a candidate agent for treating a disease or condition related to oxidative stress and/or oxidative damage. For example, a test agent that increases enzymatic activity of a SOD2 polypeptide by at least about 20%, at least about 25%, at least about 50%, at least about 75%, at least about 2-fold, at least about 2.5-fold, at least about 5-fold, at least about 10-fold, or more than 10-fold, compared to the enzymatic activity of the SOD2 polypeptide in the absence of the test agent, is considered a candidate agent for treating a disease or condition related to oxidative stress and/or oxidative damage.

In some embodiments, a test compound of interest has an $EC_{50}$ of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

Enzymatic activity of a SOD2 polypeptide can be determined using any known method, where a suitable method includes that described in Schisler and Singh (1985) *Biochem. Genet.* 23:291. Other suitable assays include those described in Weydert and Cullen (2010) *Nature Protocols* 5:51; Segura-Aguilar (1993) *Chem. Biol. Interact.* 86:69. As one non-limiting example, hydrogen peroxide formed by SOD2 is quantitated using a coupled reaction where horseradish peroxidase catalyzes the formation of a fluorescent product, 6,6'-diOH-(1,1'-biphenyl)-3,3'-diacetic acid, from 4-OH-phenylacetic acid and hydrogen peroxide. As another non-limiting example, superoxide radical ions, generated by xanthine oxidase conversion of xanthine to uric acid and hydrogen peroxide, convert nitro blue tetrazolium (NBT) to NBT-diformazan, which absorbs light at 560 nm; SOD2, which uses the superoxide ions as substrate, reduces the superoxide ion concentration and thereby lowers the rate of NBT-diformazan formation. The extent of reduction in the appearance of NBT-diformazan provides a measure of SOD activity.

A candidate agent can be assessed for any cytotoxic activity it may exhibit toward a living cell, using well-known assays, such as trypan-blue dye exclusion, an MTT (3-(4,5-dimethylthiazol-2-yl)-2,5-diphenyl-2 H-tetrazolium bromide) assay, and the like. Agents that do not exhibit cytotoxic activity are considered candidate agents.

In many embodiments, the screening method is carried out in vitro, in a cell-free assay. In some embodiments, the in vitro cell-free assay will employ a purified SOD2 polypeptide, where "purified" refers to free of contaminants or any other undesired components. Purified SOD2 polypeptide that is suitable for a subject screening method is at least about 50% pure, at least about 60% pure, at least about 70% pure, at least about 75% pure, at least about 80% pure, at least about 85% pure, at least about 90% pure, at least about 95% pure, at least about 98% pure, at least about 99% pure, or greater than 99% pure.

Purified SOD2 polypeptide will in some embodiments be stabilized by addition of one or more stabilizing agents, to maintain enzymatic activity. In some embodiments, a solution of purified SOD2 polypeptide comprises an aqueous solution comprising a SOD2 polypeptide and from about 10% to about 50% glycerol, e.g., from about 10% to about 15%, from about 15% to about 20%, from about 20% to about 25%, from about 25% to about 30%, from about 30% to about 35%, from about 35% to about 40%, from about 40% to about 45%, or from about 45% to about 50% glycerol. In some embodiments, a solution comprising a SOD2 polypeptide further comprises one or more of a chelating agent (e.g., EDTA or EGTA); salts such as NaCl, $MgCl_2$, KCl, and the like; buffers, such as a Tris buffer, phosphate-buffered saline, sodium pyrophosphate buffer, and the like; one or more protease inhibitors; and the like.

A SOD2 polypeptide suitable for use in a subject screening method can comprise an amino acid sequence having at least about 85%, at least about 90%, at least about 95%, at least about 98%, at least about 99%, or 100%, amino acid sequence identity to the amino acid sequence of a SOD2 polypeptide as depicted in FIG. 5.

A SOD2 polypeptide suitable for use in a subject screening method can comprise an amino acid sequence having at least about 85%, at least about 90%, at least about 95%, at least about 98%, at least about 99%, or 100%, amino acid sequence identity to the amino acid sequence of a subject variant SOD2 polypeptide.

A SOD2 polypeptide is readily prepared in a variety of host cells such as unicellular microorganisms, or cells of multicellular organisms grown in in vitro culture as unicellular entities. Suitable host cells include bacterial cells such as *Escherichia coli*; yeast cells such as *Saccharomyces cerevisiae, Pichia pastoris, Hansenula polymorpha, Kluyveromyces lactis, Yarrowia lipolytica, Candida utilis, Schizosaccharomyces pombe*, and the like; insect cells such as *Drosophila melanogaster* cells; amphibian cells such as Xenopus cells; mammalian cells, such as CHO cells, 3T3 cells, and the like.

In some embodiments, the in vitro cell-free assay will employ a fusion protein, comprising a SOD2 polypeptide fused in-frame to a fusion partner. In some embodiments, the fusion partner is attached to the amino terminus of the SOD2 polypeptide. In other embodiments, the fusion partner is attached to the carboxyl terminus of the SOD2 polypeptide. In other embodiments, the fusion partner is fused in-frame to the SOD2 polypeptide at a location internal to the SOD2 polypeptide. Suitable fusion partners include immunological tags such as epitope tags, including, but not limited to, hemagglutinin, FLAG, and the like; proteins that provide for a detectable signal, including, but not limited to, fluorescent proteins, enzymes (e.g., β-galactosidase, luciferase, horse radish peroxidase, etc.), and the like; polypeptides that facilitate purification or isolation of the fusion protein, e.g., metal ion binding polypeptides such as 6His tags (e.g., SOD2/6His), glutathione-S-transferase, and the like; polypeptides that provide for subcellular localization; and polypeptides that provide for secretion from a cell.

In some embodiments, the fusion partner is an epitope tag. In some embodiments, the fusion partner is a metal chelating peptide. In some embodiments, the metal chelating peptide is a histidine multimer, e.g., $(His)_6$. In some embodiments, a $(His)_6$ multimer is fused to the amino terminus of a SOD2 polypeptide; in other embodiments, a $(His)_6$ multimer is fused to the carboxyl terminus of a SOD2 polypeptide. The $(His)_6$-SOD2 fusion protein is purified using any of a variety of available nickel affinity columns (e.g. His-bind resin, Novagen).

In some embodiments, a subject screening method is carried out in vitro in a cell, e.g., a cell grown in cell culture as a unicellular entity. Suitable cells include, e.g., eukaryotic cells, e.g., mammalian cells such as CHO cells 293 cells, 3R3 cells, and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Experimental Procedures

Mice $SIRT3^{-/-}$ mice have been described (Lombard et al., 2007). All mice were housed on a 12:12-hr light:dark cycle at 25° C. Six-month-old animals (n=8) were either fed ad libitum (AL) or subjected to a 30% calorie restriction (CR) diet, which was provided daily for 6 months. Respiratory exchange ratio, physical activity and oxygen consumption were measured in metabolic cages (Columbus Instruments) for 48 hours (the first day for acclimation and the second day for experiment), according to the manufacturer's instruction. Mice were weighed before and after being placed in the cages, and were fed their allotted meals at the time they were placed in the cages. Measurements were taken every 10 minutes. All animal procedures were in accordance with the animal care committee at the University of California, Berkeley.

RNA and Protein Preparation and Analysis:

Total RNA was extracted from tissues by TRIZOL (Invitrogen) and was further purified with RNeasy mini-kit (Qiagen). For real-time polymerase chain reaction (PCR) analysis, cDNA was synthesized from total RNA by SuperScript III reverse transcriptase (Invitrogen) with random primers. cDNA was subjected to PCR analysis with gene-specific primers in the presence of CYBR green (Bio-rad). Relative mRNA abundance was obtained by normalization to cyclophilin A or glyceraldehyde-3-phosphate dehydrogenase (GAPDH) levels.

Proteins from mouse tissues were extracted in lysis buffer (50 mM Tris-Cl pH7.5, 150 mM NaCl, 10% glycerol, 2 mM $MgCl_2$, 1 mM dithiothreitol (DTT) and 1% NP40) supplemented with a complete protease inhibitor cocktail (Roche). Protein extracts were subjected to centrifugation at 14,000 rpm for 10 min. Protein lysates were precleared with protein A beads for 30 min before immunoprecipitation with specified antibodies for 2 hr—overnight. Immunoprecipitates were extensively washed with lysis buffer and eluted with 100 mM glycine, pH 3.0. Anti-long-chain acyl CoA dehydrogenase (Anti-LCAD) antibody. Acetyl-lysine antibody (Cell signaling, BioLegend). Anti-SOD2 antibody (Santa Cruz Biotechnology). Anti-Flag antibody (Sigma).

Lentiviral Production and Transduction

SIRT3 and SOD2 were cloned into pFUGW lentiviral vector. Lentiviruses were produced by transient transfection of pFUGW and packaging vectors into 293T cells with lipofectamine. Lentiviruses were harvested 48 h posttransfection and filtered through 0.22-μm-pore cellulose acetate filters.

Virus containing media was mixed with fresh media (1:1), and added to MEF cells in the presence of 8 µg/ml polybrene.

Measurement of Mitochondrial Superoxide Levels

Cells were incubated with 3 µM of Mito-SOX at 37° C. for 15 min prior to flow cytometry analysis.

Enzyme Assays:

Long-chain acyl CoA dehydrogenase (LCAD) activity was measured as previously described (Dommes and Kunau, 1976; Izai et al., 1992). The reaction mixture contained 50 mM potassium phosphate, pH 7.4, 35 µM 2,6-dichlorophenolindophenol (DCPIP), 1 mM N-ethylmaleimide (NEM), 1.6 mM phenazine methosulfate (PMS) and 500 µg liver lysate with or without 50 µM palmitoyl-CoA. OD600 was measured with Spectramax 190 (Molecular Devices). AOD600 values derived from reactions in the absence of palmitoyl-coA was considered as background.

Superoxide dismutase activity was measured as the inhibition of nitroblue tetrazolium (NBT) reduction in a xanthine-xanthine oxidase system. The assay was performed as described (Schisler and Singh, 1985), and SOD2 specific activity was determined in the presence of 5 mM sodium cyanide.

Carbonyl Content Measurement:

Protein carbonyls were spectrophotometrically quantified with a carbonyl specific reagent, 2,4-dinitrophenylhydrazine (DNPH) (Levine et al., 1994). Briefly, 1 ml of 0.5 mg protein was treated with 200 µl of 10 mM of DNPH (dissolved in 2M HCl) for 1 h, and then precipitated by 10% trichloroacetic acid. The pellets were washed with 1:1 (v/v) ethanol:ethyl acetate for 3 times, and solublized in 0.5 ml 0.2% SDS, 20 mM Tris-Cl, pH 6.8. Protein concentration in the final solution was then determined with a BCA kit (Piercenet), and the absorbance at 360 nm was measured to calculate the carbonyl content. Protein samples treated with HCl, but not with DNPH were used as blanks.

Glutathione Redox Measurement:

Glutathione was measured in mitochondrial fractions isolated from liver (Rebrin et al., 2003). The GSH:GSSG ratio was determined by Glutathione Assay Kit (BioVision), following the manufacturer's instructions.

Fatty Acid Oxidation Assay:

Liver sections (0.4 g in total) (Huang et al., 2006) or isolated primary white adipocytes (100 µl) (Ahmadian et al., 2009) were incubated with 1 ml of Krebs-Ringer buffer supplemented with 3 mM glucose, 1% BSA and [$^{14}$C]palmitic acid (0.2 µCi/ml) for 30 min or 1 h respectively at 37° C. with gentle shaking. The buffer was then acidified with 200 µl of $H_2SO_4$ (0.5N) and maintained sealed at 37° C. for an additional 30 min. $^{14}CO_2$ was trapped by 200 µl of 2-phenylethylamine/methanol (1:1 ratio) and radioactivity was quantified by liquid scintillation.

HNE Measurement:

HNE levels were measured in indicated liver samples with an OxiSelect™ HNE-His Adduct ELISA Kit (Cell Biolabs, Inc. San Diego, Calif.) following the instructions.

Statistical Analysis:

Student's t-test was used for statistic analysis and null hypotheses were rejected at 0.05.

Results

Reduction of Oxidative Stress and Damage by Calorie Restriction Requires SIRT3

We fed SIRT3 knockout (KO) mice (Lombard et al., 2007) and wild-type (WT) littermates a CR diet for 6 months. Food allotted for CR mice was 70% of the ad libitum (AL) values and was administered once daily. We first analyzed SIRT3 expression in mice fed an AL or CR diet. SIRT3 protein levels were higher in livers and white adipose tissues (WATs) of CR mice than AL controls (FIG. 1A). The CR-induced SIRT3 upregulation likely occurs at the transcriptional level, since SIRT3 mRNA was also increased (1.4-fold for liver and 3.2-fold for WAT) (FIG. 1B). Increased SIRT3 expression has also been observed in muscle and brown adipose tissue of CR mice (Palacios et al., 2009; Shi et al., 2005). CR also induces an increase in mitochondrial NAD levels (Nakagawa et al., 2009), suggesting that SIRT3 activity is likely to be upregulated during CR.

To investigate whether SIRT3 is required for CR to reduce oxidative stress, we compared oxidative damage to proteins and lipids, as well as the glutathione redox state (the GSH:GSSG ratio), a common measure of oxidative stress, between WT and SIRT3 KO mice fed AL or CR diets. Consistent with earlier reports, CR significantly reduced oxidative damage and stress in WT mice (Merry, 2004; Rebrin et al., 2003), as shown by levels of 4-hydroxy-2-nonenal (HNE), a marker for lipid peroxidation (FIG. 1C), protein carbonyl content, a protein oxidative modification (FIG. 1D), and the GSH:GSSG ratio (FIG. 1E). However, the reduction in oxidative stress and damage under CR was not observed in SIRT3 KO mice (FIG. 1C-E), suggesting that SIRT3 is required for reducing oxidative stress during CR. Consistent with these results, overexpression of SIRT3 is sufficient to reduce cellular ROS levels (Shi et al., 2005).

Figure 2:
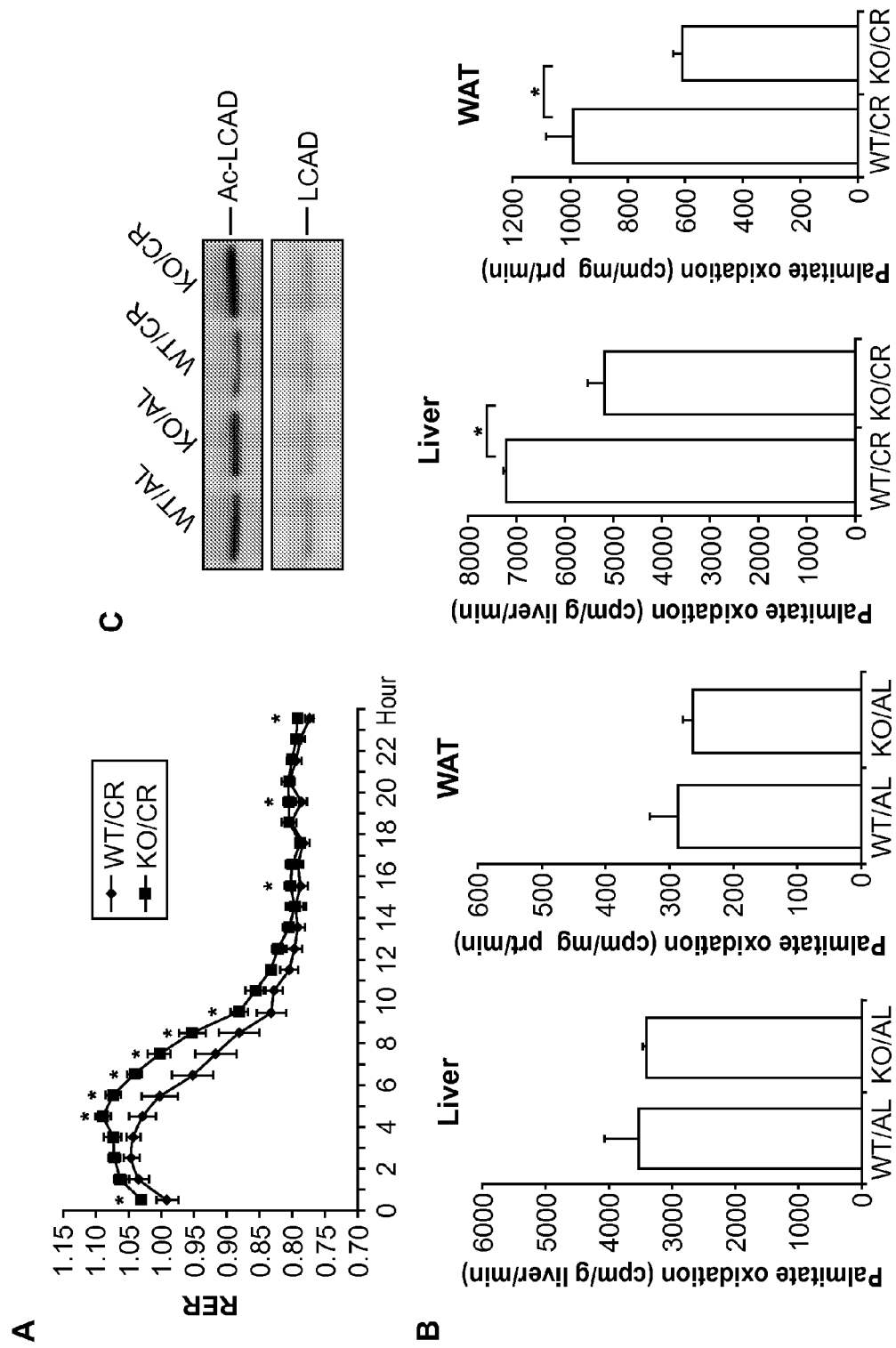
FIGS. 2A-E depict the role of SIRT3 in calorie restriction-induced metabolic switch to fatty acid oxidation.
Figure 2:
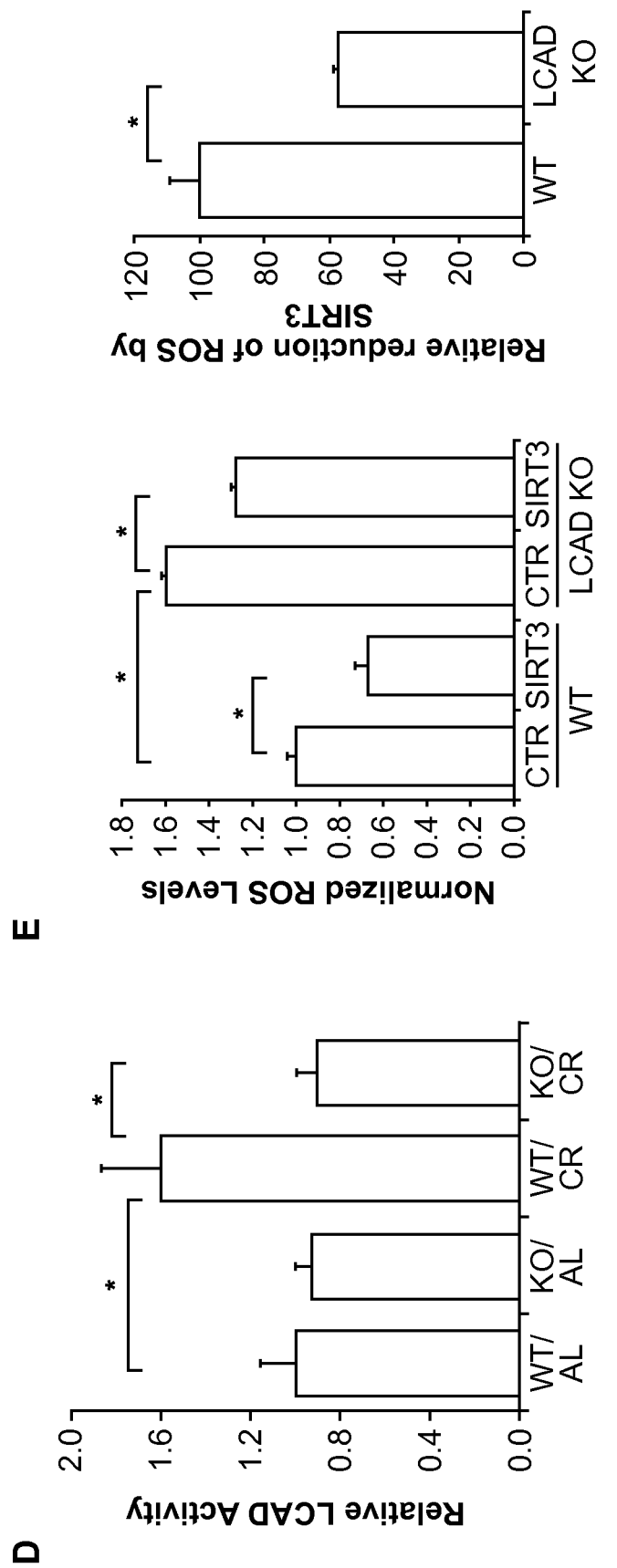

SIRT3 is Required for the Calorie Restriction-Induced Metabolic Switch to Fatty Acid Oxidation Next, we investigated the mechanism by which SIRT3 reduces oxidative stress during CR. CR was hypothesized to reduce ROS production by triggering a metabolic switch from glucose to fatty acid oxidation (FAO) (Guarente, 2008). Compared to glucose oxidation, FAO during respiration preferably bypasses a major site of ROS production, the complex I of the electron transport chain. To test whether SIRT3 reduces ROS production by triggering the metabolic switch from glucose to FAO during CR, we compared calorie restricted WT and SIRT3 KO mice for their respiratory exchange ratio (RER), an indicator of which fuel (carbohydrate or fat) is being metabolized to supply the body with energy. The RER of the CR mice was recorded for one feeding cycle (24 hours) starting from when the mice were provided with their daily quota of food. Six hours after feeding, the RER for calorie restricted WT mice dropped below 1, indicating a shift from glucose to FAO (FIG. 2A). However, this shift was delayed 2 hours in calorie restricted SIRT3 KO mice, and the RER for calorie restricted SIRT3 KO mice remained higher than WT controls until 10 hours after feeding. These observations indicate that SIRT3 can influence the metabolic switch to FAO that normally occurs during CR. To further confirm that calorie restricted SIRT3 KO mice are deficient in FAO, we directly measured the beta-oxidation rates for long-chain fatty acids in livers and WATs. The beta-oxidation rates, determined by the oxidation of palmitate to $CO_2$ (Ahmadian et al., 2009), were decreased by 40% in calorie restricted SIRT3 KO mice in comparison to WT controls 7 hours after feeding (FIG. 2B).

Despite the defects in FAO, calorie restricted SIRT3 KO mice had comparable metabolic rate as WT controls, measured by daily oxygen consumption normalized by their body weight. Consistently, calorie restricted WT and SIRT3 KO mice had comparable physical activity, food intake, and body weight, indicating that interfering with SIRT3 function does not affect the metabolic rate and that SIRT3 does not reduce oxidative stress by changing the metabolic rate during CR.

Long-Chain Acyl CoA Dehydrogenase is Activated via SIRT3 Deacetylation during Calorie Restriction, Contributing to the Reduction of Cellular ROS SIRT3 increases FAO during short-term fasting by deacetylating and activating long-chain acyl CoA dehydrogenase (LCAD), the enzyme that catalyzes the first step of beta-oxidation (Hirschey et al., 2010). To test whether SIRT3 regulates the metabolic switch to FAO during CR by deacetylating and activating LCAD, we compared acetylation levels of LCAD and its enzymatic activity in the livers of WT and SIRT3 KO mice fed AL or CR diets. To assess the acetylation levels of LCAD in mouse tissues, endogenous proteins were immunoprecipitated with anti-acetyllysine antibody and analyzed by western blotting with LCAD specific antibody. LCAD acetylation was decreased during CR in WT but not SIRT3 KO mice (FIG. 2C). Endogenous LCAD activity was determined using tissue lysates in a well-established assay by quantifying the oxidation of palmitoyl-CoA (Izai et al., 1992). In parallel to its acetylation status, we observed a 50% increase in enzymatic activity of LCAD in WT but not SIRT3 KO mice during CR (FIG. 2D). Thus, hyperacetylation and inactivation of LCAD might account for decreased FAO in calorie restricted SIRT3 KO mice.

To determine whether SIRT3 requires LCAD to mediate the reduction of cellular ROS, we overexpressed SIRT3 in WT or LCAD-deficient mouse embryonic fibroblasts (MEFs) via lentiviral transduction, and quantified cellular ROS levels by MitoSox, a mitochondrial superoxide indicator. Endogenous ROS levels in LCAD-deficient MEFs were higher than those in WT controls (FIG. 2E), consistent with the notion that dysregulation of FAO increases oxidative stress (Kabuyama et al., 2010). SIRT3 overexpression reduced cellular ROS levels by 30% in WT MEFs. In contrast, the reduction of ROS mediated by SIRT3 overexpression was 40% lower in LCAD-deficient MEFs than in WT controls. These results indicate that SIRT3 reduces cellular ROS via LCAD. However, other mechanism(s) also contribute to this process.

SIRT3 Activates SOD2 via Deacetylation

Figure 3:
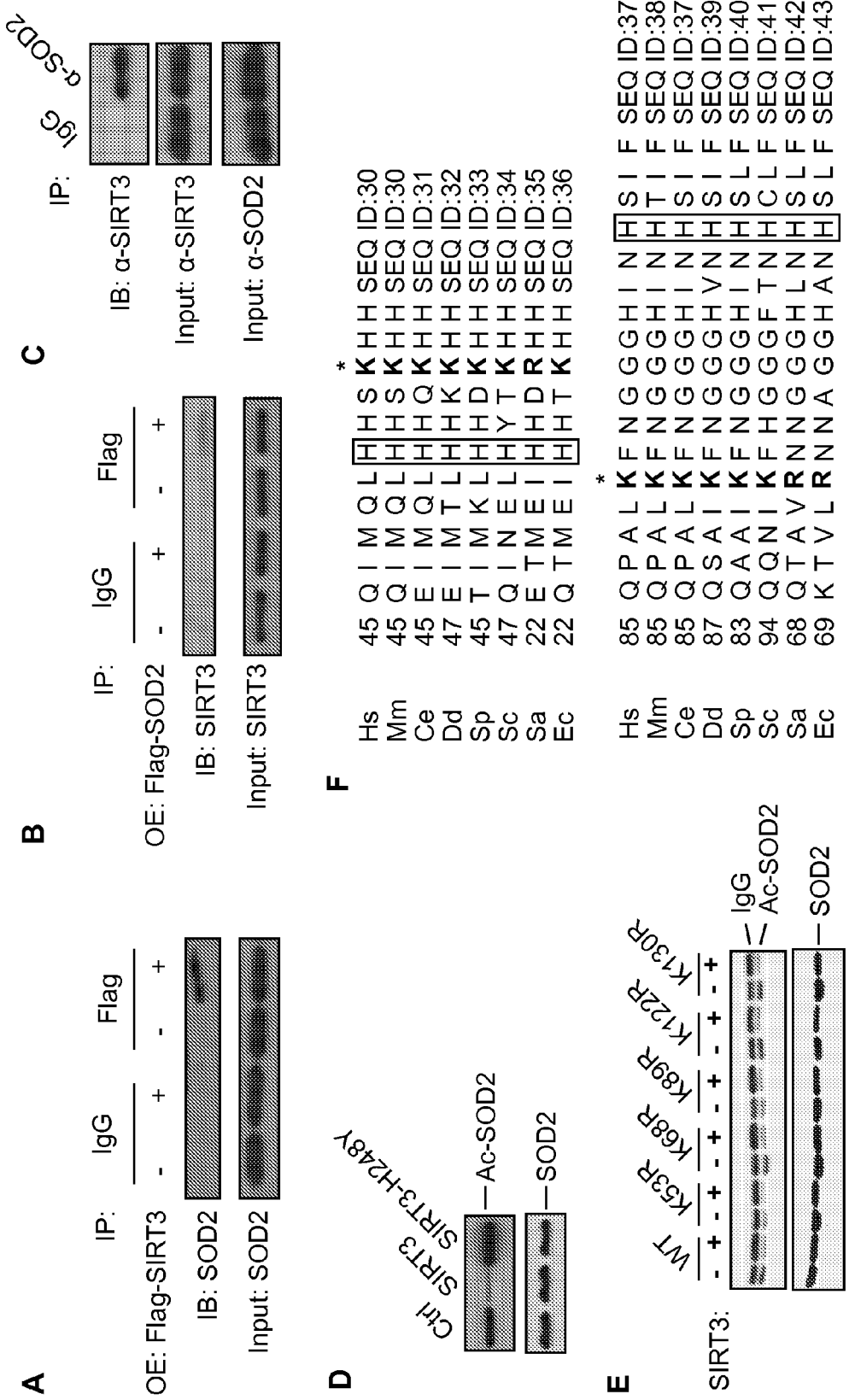
FIGS. 3A-K depict SIRT3-mediated reduction of cellular ROS levels by deacetylation and activation of SOD2.
Figure 3:
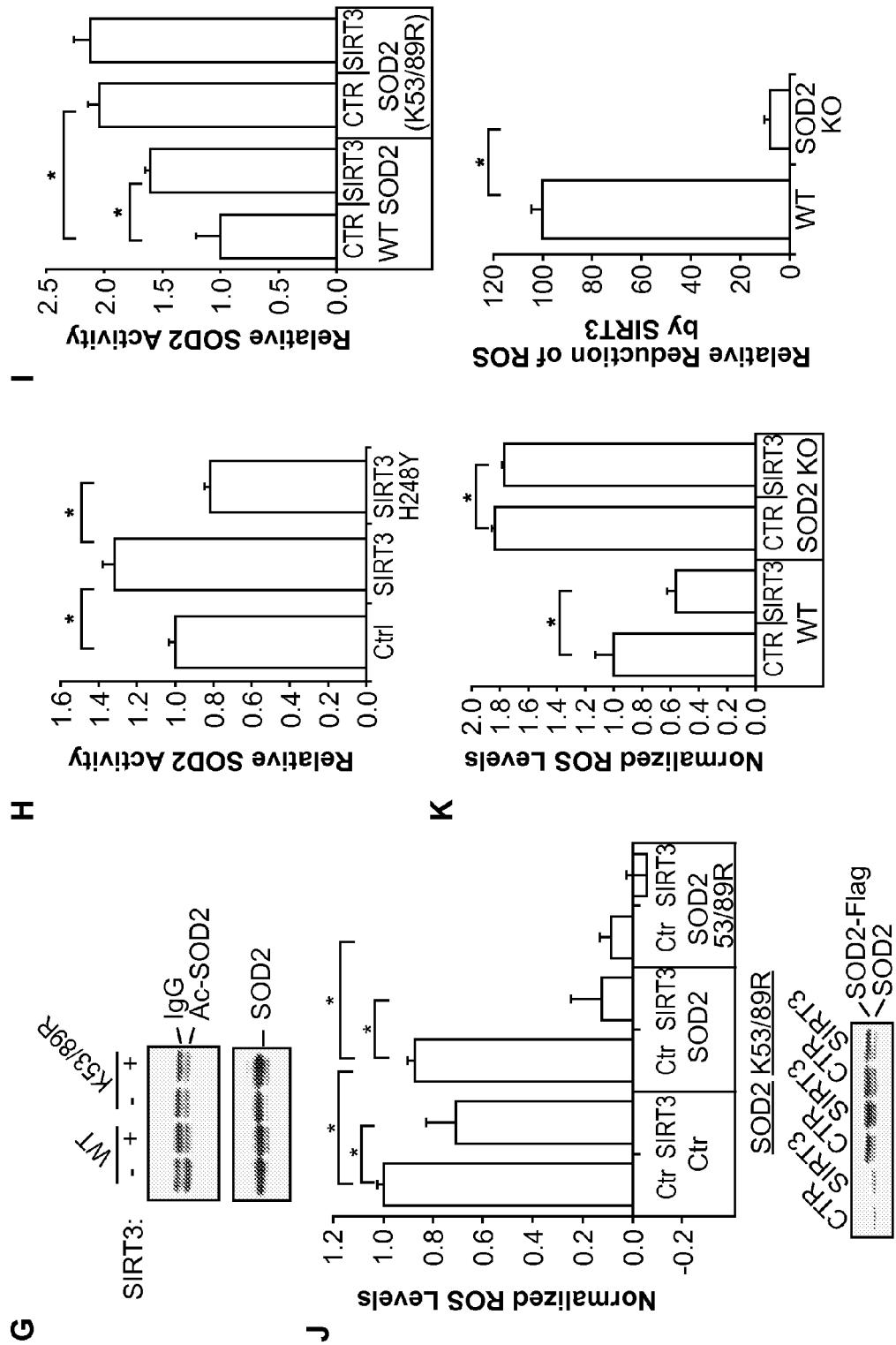

Cellular ROS levels represent the integration of two distinct processes: ROS production during respiration and ROS detoxification by antioxidants (Balaban et al., 2005). We next investigated whether SIRT3 also reduces oxidative stress by promoting ROS detoxification. SOD2 was identified in screens of acetylated peptides (Choudhary et al., 2009; Kim et al., 2006; Schwer et al., 2009). Because SOD2 is located in the mitochondria, we tested the possibility that SIRT3 regulates its acetylation state. To test whether SIRT3 interacts with SOD2, we overexpressed Flag-tagged SIRT3 in 293T cells and SIRT3-associated proteins were immunopurified (anti-Flag). The association of SOD2 with SIRT3 was detected by western blotting with SOD2 antibody (FIG. 3A). Additionally, we also transfected Flag-tagged SOD2 into 293T cells and the presence of SIRT3 in the immunopurified SOD2 complex was confirmed by western blotting with SIRT3 antibody (FIG. 3B). Finally, we examined whether the interaction between SIRT3 and SOD2 is physiologically relevant by carrying out immunoprecipitation with liver extracts. SIRT3 was co-immunoprecipitated with SOD2 antibody (FIG. 3C).

To test whether SIRT3 deacetylates SOD2, we co-transfected Flag-tagged SOD2 with SIRT3 or enzymatically inactive SIRT3-H248Y into 293T cells. Acetylation levels for SOD2 were measured after immunoprecipitation by western blotting with anti-acetyllysine antibody. SIRT3, but not SIRT3-H248Y, deacetylated SOD2 (FIG. 3D). To identify which lysine residue(s) on SOD2 are targeted by SIRT3 for deacetylation, we mutated lysines (K68, K122, and K130) that have been shown to be acetylated in mass spectrometry-based acetylation proteomic surveys (Choudhary et al., 2009; Kim et al., 2006; Schwer et al., 2009). SOD2 mutants were overexpressed in 293T cells with or without SIRT3, immunopurified, and their acetylation status was measured. Surprisingly, mutating these three lysine residues did not significantly reduce the overall acetylation levels of SOD2 (FIG. 3E). Additionally, SIRT3 co-expression reduced acetylation levels of these three SOD2 mutants, indicating that these three lysines are unlikely to be the major acetylation sites on SOD2.

Protein sequence alignment studies showed that two lysines (K53 and K89) adjacent to the active site of SOD2 are highly conserved across species (FIG. 3F). Acetylation levels of SOD2 were decreased when these two lysines were mutated individually (K53R and K89R) or simultaneously (K53/89R) (FIG. 3E, G). SIRT3 co-expression further decreased acetylation levels of K53R and K89R, but not K53/89R. Collectively, these studies identified K53 and K89 as the acetylation sites on SOD2 targeted by SIRT3.

To determine whether the acetylation state of SOD2 modifies its enzymatic activity, Flag-tagged SOD2 was overexpressed in 293T cells with SIRT3 or with SIRT3-H248Y, purified by immunoprecipitation, and their enzymatic activity was determined by measuring superoxide conversion colorimetrically (Schisler and Singh, 1985). Overexpression of WT SIRT3 decreased the acetylation of SOD2 (FIG. 3D, E, G) and significantly increased its enzymatic activity (FIG. 3H). In contrast, overexpression of SIRT3-H248Y had the opposite effect. Additionally, the enzymatic activity of SOD2 K53/89R, which has two acetylation sites mutated to arginine to mimic the constitutively deacetylated state, was 100% higher than the WT control and SIRT3 did not further increase its enzymatic activity (FIG. 3I). Thus, SIRT3 promotes the enzymatic activity of SOD2 by deacetylating two critical lysine residues adjacent to the active site. Conceivably, these two lysine residues, when exposed, increase the positive charge around the active site and improve the efficiency of trapping the negatively charged superoxide.

SIRT3 Reduces Cellular ROS Levels by Deacetylating SOD2

To determine whether SIRT3 reduces cellular ROS levels by deacetylating SOD2, we overexpressed SOD2 or SOD2 K53/89R with or without SIRT3 into SIRT3 KO MEFs and assessed cellular ROS levels. Surprisingly, overexpression of SOD2 6-fold above the endogenous levels only marginally decreased cellular ROS levels (10%) (FIG. 3J). However, co-expression of SIRT3 and SOD2 almost depleted cellular ROS. Additionally, the constitutively deacetylated SOD2 (K53/89R) alone also diminished cellular ROS. These results indicate that increasing SOD2 expression is not sufficient to effectively reduce cellular ROS until it is activated via deacetylation by SIRT3.

To determine to what extent SOD2 contributes to the reduction of cellular ROS mediated by SIRT3, we overexpressed SIRT3 in WT and SOD2 KO MEFs via lentiviral transduction and assessed cellular ROS levels. Reduction of cellular ROS mediated by SIRT3 was decreased 90% in SOD2 KO MEFs compared to WT controls (FIG. 3K), indicating that SOD2 is the major downstream mediator of SIRT3 in reducing cellular ROS.

SOD2 is Activated by SIRT3-mediated Deacetylation during Calorie Restriction

Figure 4:
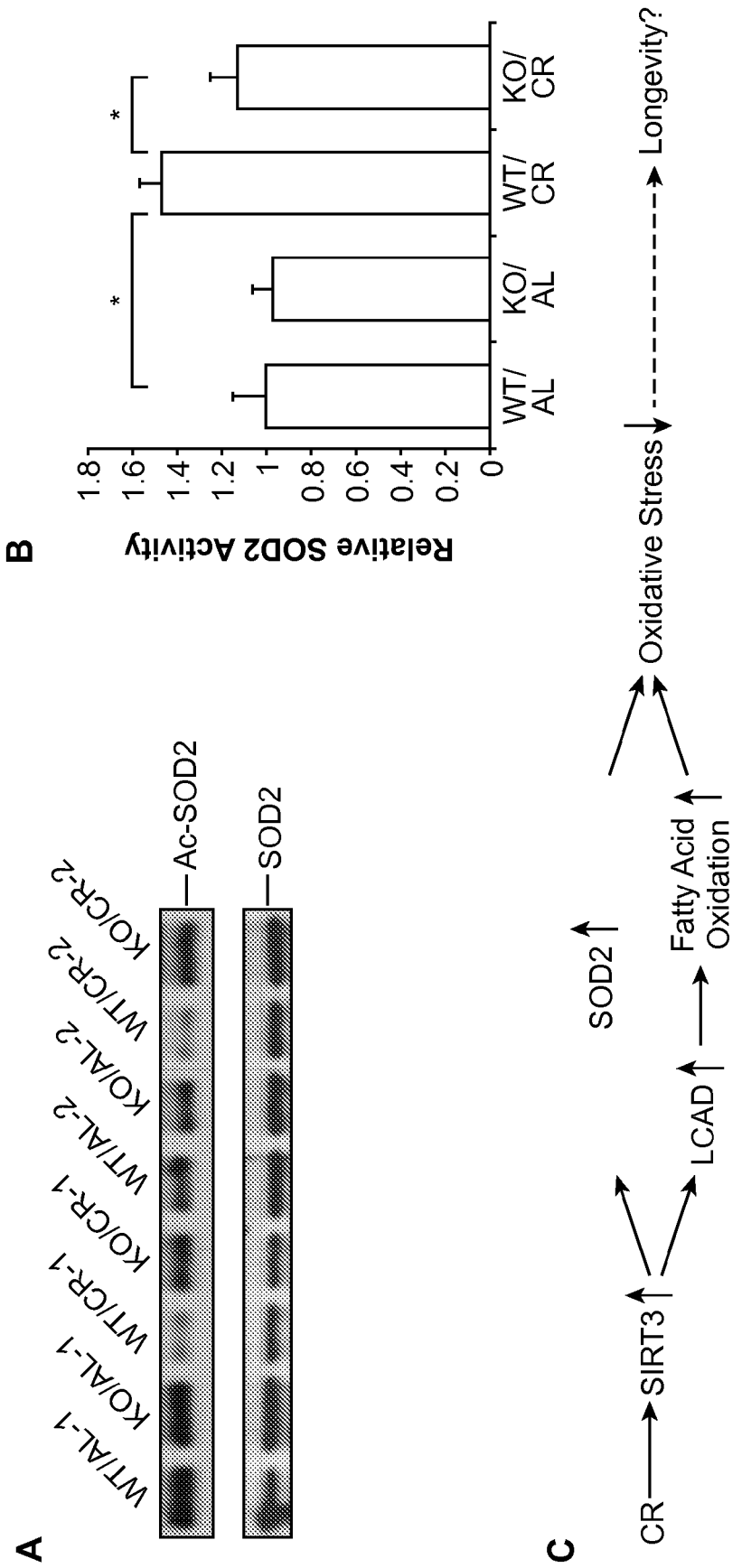
FIGS. 4A-C depict SIRT3 dependence of activation of SOD2 during calorie restriction.

Based on the results that SIRT3 is induced by CR and that SIRT3 deacetylates and activates SOD2, we speculated that SIRT3 might deacetylate SOD2 and increase its antioxidative activity in CR animals. We compared the acetylation levels of SOD2 and its antioxidative activity in WT and SIRT3 KO mice fed AL or CR diets. To assess the acetylation levels of SOD2 in mouse tissues, endogenous proteins were immunoprecipitated with anti-SOD2 antibody and analyzed by western blotting using acetyl-lysine antibody. Endogenous SOD2 was acetylated and became deacetylated during CR in WT mice (FIG. 4A). However, CR-induced SOD2 deacetylation was not observed in SIRT3 KO mice, demonstrating that SIRT3 is necessary for SOD2 deacetylation during CR. We next determined endogenous SOD2 activity using tissue lysates as described (Schisler and Singh, 1985). CR induced a 50% increase in SOD2 activity in the WATs of WT mice (FIG. 4B) and a modest but significant increase in liver. Importantly, this increase in SOD2 activity under CR was lost in SIRT3 KO mice (FIG. 4B). These results suggest that during CR, SIRT3 reduces oxidative stress by activating SOD2 and promoting the detoxification of ROS.

FIGS. 1A-E. Reduction of oxidative stress and damage by calorie restriction requires SIRT3. (A, B) SIRT3 is upregulated during calorie restriction. The expression levels of SIRT3 in livers and WATs of mice fed AL or calorie restricted were determined by western blotting (A) or RT-PCR (B). n=5. *$P<0.05$. (C, D, E) Reduction of oxidative stress and damage by CR is dependent on SIRT3. Liver lysates from WT and SIRT3 KO mice fed an AL or CR diet were assayed for lipid peroxidation (C), protein carbonyl formation (D), and the GSH:GSSG ratio (E).

FIGS. 2A-E. Calorie restriction induces a metabolic switch to fatty acid oxidation dependent on SIRT3. (A, B) SIRT3 KO mice are defective in the metabolic switch to FAO during CR. (A) Calorie restricted WT and SIRT3 KO mice were housed in metabolic chambers for 24 hours for acclimation. Respiratory exchange ratio (RER) was measured in metabolic chambers for one feeding cycle (24 hours) starting from when the mice were provided with daily quota of food. n=8. (B) Livers and WATs of WT and SIRT3 KO mice fed an AL or CR diet were harvested 7 hours after feeding and beta-oxidation rates in these tissues were quantified by the conversion of palmitate to $CO_2$. (C, D) SIRT3 deacetylates and activates LCAD in CR mice. The acetylation levels of LCAD (C) and its enzymatic activity (D) in the liver lysates from WT and SIRT3 KO mice fed an AL or CR diet were determined. Liver tissues were harvested from CR mice 7 hours after feeding. Acetylated LCAD was isolated from the liver lysate by immunoprecipitation with anti-acetyl-lysine antibody followed by western blotting with anti-LCAD antibody. LCAD activity was determined as described (Izai et al., 1992). (E) SIRT3 reduces cellular ROS via LCAD. SIRT3 was overexpressed in WT and LCAD KO MEFs via lentiviral transduction and the cellular ROS levels were quantified by MitoSox staining.

FIGS. 3A-K. SIRT3 reduces cellular ROS levels by deacetylating and activating SOD2. (A, B, C) SIRT3 physically interacts with SOD2 in vivo. (A) Flag-tagged SIRT3 was transfected into 293T cells, immunopurified, followed by western blotting with anti-SOD2. (B) Flag-tagged SOD2 was transfected into 293T cells. The association of SIRT3 with immunopurified Flag-SOD2 was detected by western blotting with anti-SIRT3 antibody. (C) Endogenous SOD2 was immunopurified from liver lysates with anti-SOD2 antibody, followed by western blotting with anti-SIRT3 antibody. (D-G) SIRT3 deacetylates two critical lysine residues on SOD2 in vivo. (D, E, G) Flag-tagged SOD2 or SOD2 mutants were co-transfected with a control vector, SIRT3, or SIRT3-H248Y into 293T cells. Immunopurified Flag-tagged SOD2 was examined for its acetylation levels by western blotting with anti-acetyl-lysine antibody. (F) Sequence alignment of SOD2 from various species. Residues (H50 and H98) coordinating the metal center are shaded. Conserved lysines (K53 and K89) are in bold. (H, I) SIRT3 activates SOD2 by deacetylating two critical lysine residues in vivo. Flag-tagged SOD2 or SOD2 K53/89R was co-transfected with a control vector, SIRT3, or SIRT3-H248Y into 293T cells. The antioxidative activity of immunopurified SOD2 was determined by conversion of superoxide colormetrically as described (Schisler and Singh, 1985). (J) SIRT3 reduces cellular ROS by deacetylating SOD2. SOD2 or SOD2 K53/89R mutant was overexpression with or without SIRT3 in SIRT3 KO MEFs, and cellular ROS levels were determined by MitoSox staining. (K) SIRT3 reduces cellular ROS via SOD2. SIRT3 was overexpressed in WT and SOD2 KO MEFs via lentiviral transduction and cellular ROS levels were quantified by MitoSox staining.

FIGS. 4A-C. Activation of SOD2 during calorie restriction is SIRT3 dependent. (A) SIRT3 deacetylates SOD2 in CR mice. The acetylation levels of SOD2 in WT and SIRT3 KO mice fed an AL or CR diet were determined. Endogenous acetylated SOD2 was isolated by immunoprecipitation with anti-SOD2 antibody followed by western blotting with anti-acetyl-lysine antibody. (B) SIRT3 increases the antioxidative activity of SOD2 in CR mice. The antioxidative activity of SOD2 in WATs of WT and SIRT3 KO mice fed an AL or CR diet were determined (Schisler and Singh, 1985). (C) A proposed model on how SIRT3 mediates the CR response.

REFERENCES

Ahmadian, M., Duncan, R. E., Varady, K. A., Frasson, D., Hellerstein, M. K., Birkenfeld, A. L., Samuel, V. T., Shulman, G. I., Wang, Y., Kang, C., and Sul, H. S. (2009). Adipose overexpression of desnutrin promotes fatty acid use and attenuates diet-induced obesity. Diabetes 58, 855-866.

Baba, T., Shimizu, T., Suzuki, Y., Ogawara, M., Isono, K., Koseki, H., Kurosawa, H., and Shirasawa, T. (2005). Estrogen, insulin, and dietary signals cooperatively regulate longevity signals to enhance resistance to oxidative stress in mice. J Biol Chem 280, 16417-16426.

Balaban, R. S., Nemoto, S., and Finkel, T. (2005). Mitochondria, oxidants, and aging. Cell 120, 483-495.

Chen, D., Steele, A. D., Lindquist, S., and Guarente, L. (2005). Increase in activity during calorie restriction requires Sirt1. Science 310, 1641.

Choudhary, C., Kumar, C., Gnad, F., Nielsen, M. L., Rehman, M., Walther, T. C., Olsen, J. V., and Mann, M. (2009). Lysine acetylation targets protein complexes and co-regulates major cellular functions. Science 325, 834-840.

Cohen, D. E., Supinski, A. M., Bonkowski, M. S., Donmez, G., and Guarente, L. P. (2009). Neuronal SIRT1 regulates endocrine and behavioral responses to calorie restriction. Genes Dev 23, 2812-2817.

Cohen, H. Y., Miller, C., Bitterman, K. J., Wall, N. R., Hekking, B., Kessler, B., Howitz, K. T., Gorospe, M., de Cabo, R., and Sinclair, D. A. (2004). Calorie restriction promotes mammalian cell survival by inducing the SIRT1 deacetylase. Science 305, 390-392.

Colman, R. J., Anderson, R. M., Johnson, S. C., Kastman, E. K., Kosmatka, K. J., Beasley, T. M., Allison, D. B., Cruzen, C., Simmons, H. A., Kemnitz, J. W., and Weindruch, R. (2009). Caloric restriction delays disease onset and mortality in rhesus monkeys. Science 325, 201-204.

Colom, B., Oliver, J., Roca, P., and Garcia-Palmer, F. J. (2007). Caloric restriction and gender modulate cardiac muscle mitochondrial H2O2 production and oxidative damage. Cardiovasc Res 74, 456-465.

Dommes, V., and Kunau, W. H. (1976). A convenient assay for acyl-CoA-dehydrogenases. Anal Biochem 71, 571-578.

Frye, R. A. (2000). Phylogenetic classification of prokaryotic and eukaryotic Sir2-like proteins. Biochem Biophys Res Commun 273, 793-798.

Guarente, L. (2008). Mitochondria—nexus for aging, calorie restriction, and sirtuins? Cell 132, 171-176.

Hauck, S. J., Hunter, W. S., Danilovich, N., Kopchick, J. J., and Bartke, A. (2001). Reduced levels of thyroid hormones, insulin, and glucose, and lower body core temperature in the growth hormone receptor/binding protein knockout mouse. Exp Biol Med (Maywood) 226, 552-558.

Hirschey, M. D., Shimazu, T., Goetzman, E., Jing, E., Schwer, B., Lombard, D. B., Grueter, C. A., Harris, C., Biddinger, S., Ilkayeva, O. R., Stevens, R. D., Li, Y., Saha, A. K., Ruderman, N. B., Bain, J. R., Newgard, C. B., Farese, R. V., Jr., Alt, F. W., Kahn, C. R., and Verdin, E. (2010). SIRT3 regulates mitochondrial fatty-acid oxidation by reversible enzyme deacetylation. Nature 464, 121-125.

Huang, W., Dedousis, N., Bandi, A., Lopaschuk, G. D., and O'Doherty, R. M. (2006). Liver triglyceride secretion and lipid oxidative metabolism are rapidly altered by leptin in vivo. Endocrinology 147, 1480-1487.

Imai, S., Armstrong, C. M., Kaeberlein, M., and Guarente, L. (2000). Transcriptional silencing and longevity protein Sir2 is an NAD-dependent histone deacetylase. Nature 403, 795-800.

Izai, K., Uchida, Y., Orii, T., Yamamoto, S., and Hashimoto, T. (1992). Novel fatty acid beta-oxidation enzymes in rat liver mitochondria. I. Purification and properties of very-long-chain acyl-coenzyme A dehydrogenase. J Biol Chem 267, 1027-1033.

Kabuyama, Y., Suzuki, T., Nakazawa, N., Yamaki, J., Homma, M. K., and Homma, Y. (2010). Dysregulation of very long chain acyl-CoA dehydrogenase coupled with lipid peroxidation. Am J Physiol Cell Physiol 298, C107-113.

Kaeberlein, M., McVey, M., and Guarente, L. (1999). The SIR2/3/4 complex and SIR2 alone promote longevity in *Saccharomyces cerevisiae* by two different mechanisms. Genes Dev 13, 2570-2580.

Kim, H. S., Patel, K., Muldoon-Jacobs, K., Bisht, K. S., Aykin-Burns, N., Pennington, J. D., van der Meer, R., Nguyen, P., Savage, J., Owens, K. M., Vassilopoulos, A., Ozden, O., Park, S. H., Singh, K. K., Abdulkadir, S. A., Spitz, D. R., Deng, C. X., and Gius, D. SIRT3 Is a Mitochondria-localized Tumor Suppressor Required for Maintenance of Mitochondrial Integrity and Metabolism during Stress. Cancer Cell 17, 41-52.

Kim, S. C., Sprung, R., Chen, Y., Xu, Y., Ball, H., Pei, J., Cheng, T., Kho, Y., Xiao, H., Xiao, L., Grishin, N. V., White, M., Yang, X. J., and Zhao, Y. (2006). Substrate and functional diversity of lysine acetylation revealed by a proteomics survey. Mol Cell 23, 607-618.

Levine, R. L., Williams, J. A., Stadtman, E. R., and Shacter, E. (1994). Carbonyl assays for determination of oxidatively modified proteins. Methods Enzymol 233, 346-357.

Li, Y., Xu, W., McBurney, M. W., and Longo, V. D. (2008). SirT1 inhibition reduces IGF-I/IRS-2/Ras/ERK1/2 signaling and protects neurons. Cell Metab 8, 38-48.

Lin, S. J., Defossez, P. A., and Guarente, L. (2000). Requirement of NAD and SIR2 for life-span extension by calorie restriction in *Saccharomyces cerevisiae*. Science 289, 2126-2128.

Lombard, D. B., Alt, F. W., Cheng, H. L., Bunkenborg, J., Streeper, R. S., Mostoslaysky, R., Kim, J., Yancopoulos, G., Valenzuela, D., Murphy, A., Yang, Y., Chen, Y., Hirschey, M. D., Bronson, R. T., Haigis, M., Guarente, L. P., Farese, R. V., Jr., Weissman, S., Verdin, E., and Schwer, B. (2007). Mammalian Sir2 homolog SIRT3 regulates global mitochondrial lysine acetylation. Mol Cell Biol 27, 8807-8814.

Masoro, E. J., Yu, B. P., and Bertrand, H. A. (1982). Action of food restriction in delaying the aging process. Proc Natl Acad Sci USA 79, 4239-4241.

Merry, B. J. (2004). Oxidative stress and mitochondrial function with aging—the effects of calorie restriction. Aging Cell 3, 7-12.

Nakagawa, T., Lomb, D. J., Haigis, M. C., and Guarente, L. (2009). SIRT5 Deacetylates carbamoyl phosphate synthetase 1 and regulates the urea cycle. Cell 137, 560-570.

Nisoli, E., Tonello, C., Cardile, A., Cozzi, V., Bracale, R., Tedesco, L., Falcone, S., Valerio, A., Cantoni, O., Clementi, E., Moncada, S., and Carruba, M. O. (2005). Calorie restriction promotes mitochondrial biogenesis by inducing the expression of eNOS. Science 310, 314-317.

Onyango, P., Celic, I., McCaffery, J. M., Boeke, J. D., and Feinberg, A. P. (2002). SIRT3, a human SIR2 homologue, is an NAD-dependent deacetylase localized to mitochondria. Proc Natl Acad Sci USA 99, 13653-13658.

Palacios, O. M., Carmona, J. J., Michan, S., Chen, K. Y., Manabe, Y., Iii, J. L., Goodyear, L. J., and Tong, Q. (2009). Diet and exercise signals regulate SIRT3 and activate AMPK and PGC-1alpha in skeletal muscle. Aging (Albany N.Y.) 1, 771-783.

Perez, V. I., Bokov, A., Van Remmen, H., Mele, J., Ran, Q., Ikeno, Y., and Richardson, A. (2009). Is the oxidative stress theory of aging dead? Biochim Biophys Acta 1790, 1005-1014.

Rebrin, I., Kamzalov, S., and Sohal, R. S. (2003). Effects of age and caloric restriction on glutathione redox state in mice. Free Radic Biol Med 35, 626-635.

Rogina, B., and Helfand, S. L. (2004). Sir2 mediates longevity in the fly through a pathway related to calorie restriction. Proc Natl Acad Sci USA 101, 15998-16003.

Schisler, N. J., and Singh, S. M. (1985). Tissue-specific developmental regulation of superoxide dismutase (SOD-1 and SOD-2) activities in genetic strains of mice. Biochem Genet 23, 291-308.

Schriner, S. E., Linford, N. J., Martin, G. M., Treuting, P., Ogburn, C. E., Emond, M., Coskun, P. E., Ladiges, W., Wolf, N., Van Remmen, H., Wallace, D. C., and Rabinovitch, P. S. (2005). Extension of murine life span by overexpression of catalase targeted to mitochondria. Science 308, 1909-1911.

Schulz, T. J., Zarse, K., Voigt, A., Urban, N., Birringer, M., and Ristow, M. (2007). Glucose restriction extends *Caenorhabditis elegans* life span by inducing mitochondrial respiration and increasing oxidative stress. Cell Metab 6, 280-293.

Schwer, B., Eckersdorff, M., Li, Y., Silva, J. C., Fermin, D., Kurtev, M. V., Giallourakis, C., Comb, M. J., Alt, F. W., and Lombard, D. B. (2009). Calorie restriction alters mitochondrial protein acetylation. Aging Cell 8, 604-606.

Schwer, B., North, B. J., Frye, R. A., Ott, M., and Verdin, E. (2002). The human silent information regulator (Sir)2 homologue hSIRT3 is a mitochondrial nicotinamide adenine dinucleotide-dependent deacetylase. J Cell Biol 158, 647-657.

Shi, T., Wang, F., Stieren, E., and Tong, Q. (2005). SIRT3, a mitochondrial sirtuin deacetylase, regulates mitochondrial function and thermogenesis in brown adipocytes. J Biol Chem 280, 13560-13567.

Sinclair, D. A. (2005). Toward a unified theory of caloric restriction and longevity regulation. Mech Ageing Dev 126, 987-1002.

Sohal, R. S., and Weindruch, R. (1996). Oxidative stress, caloric restriction, and aging. Science 273, 59-63.

Sundaresan, N. R., Gupta, M., Kim, G., Rajamohan, S. B., Isbatan, A., and Gupta, M. P. (2009). Sirt3 blocks the cardiac hypertrophic response by augmenting Foxo3a-dependent antioxidant defense mechanisms in mice. J Clin Invest 119, 2758-2771.

Taguchi, A., Wartschow, L. M., and White, M. F. (2007). Brain IRS2 signaling coordinates life span and nutrient homeostasis. Science 317, 369-372.

Tissenbaum, H. A., and Guarente, L. (2001). Increased dosage of a sir-2 gene extends lifespan in *Caenorhabditis elegans*. Nature 410, 227-230.

Van Remmen, H., Guo, Z., and Richardson, A. (2001). The anti-ageing action of dietary restriction. Novartis Found Symp 235, 221-230; discussion 230-223.

Wallace, D. C., and Fan, W. (2009). The pathophysiology of mitochondrial disease as modeled in the mouse. Genes Dev 23, 1714-1736.

Weindruch, R. a. W., R. L. (1988). The retardation of aging and disease by dietary restriction. Yamamoto, M., Clark, J. D., Pastor, J. V., Gurnani, P., Nandi, A., Kurosu, H., Miyoshi, M., Ogawa, Y., Castrillon, D. H., Rosenblatt, K. P., and Kuro-o, M. (2005). Regulation of oxidative stress by the anti-aging hormone klotho. J Biol Chem 280, 38029-38034.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A variant superoxide dismutase-2 (SOD2) polypeptide, wherein the variant SOD2 polypeptide comprises amino acid substitutions of at least K53 and K89 compared to the amino acid sequence set forth in SEQ ID NO: 1, wherein the variant SOD2 polypeptide comprises an amino acid sequence having at least 95% amino acid sequence identity to the amino acid sequence set forth in SEQ ID NO: 1, and wherein the variant SOD2 polypeptide exhibits superoxide dismutase enzymatic activity that is at least 50% higher than the superoxide dismutase enzymatic activity of a SOD2 polypeptide comprising the amino acid sequence set forth in SEQ ID NO: 1.

2. A composition comprising the variant superoxide dismutase-2 (SOD2) polypeptide of claim 1.

3. A pharmaceutical composition comprising the variant superoxide dismutase-2 (SOD2) polypeptide of claim 1.

4. The pharmaceutical composition of claim 3, wherein the pharmaceutical composition comprises at least one food-grade component.

5. A method of reducing oxidative damage and/or oxidative stress in a cell, the method comprising contacting the cell with the variant superoxide dismutase-2 (SOD2) polypeptide of claim 1, wherein the variant SOD2 polypeptide enters the cell and reduces oxidative damage and/or oxidative stress in the cell.

6. The method of claim 5, wherein the cell is a mammalian cell.

7. A method of reducing oxidative damage and/or oxidative stress in an individual, the method comprising administering to the individual an effective amount of the variant superoxide dismutase-2 (SOD2) polypeptide of claim 1.

8. The variant SOD2 polypeptide of claim 1, wherein the variant SOD2 polypeptide comprises an amino acid sequence having at least 98% amino acid sequence identity to the amino acid sequence set forth in SEQ ID NO: 1.

9. The variant SOD2 polypeptide of claim 1, wherein the SOD2 polypeptide comprises a K53R substitution and a K89R substitution compared to the amino acid sequence set forth in SEQ ID NO: 1.

10. The variant SOD2 polypeptide of claim 1, wherein the variant SOD2 polypeptide further comprises a poly(ethylene glycol) moiety, a saccharide moiety, a carbohydrate moiety, a myristyl group, or a lipid moiety.

11. The variant SOD2 polypeptide of claim 1, wherein the variant SOD2 polypeptide further comprises a protein transduction domain.

* * * * *

SEQUENCE LISTING

```
<160> NUMBER OF SEQ ID NOS: 43

<210> SEQ ID NO 1
<211> LENGTH: 222
<212> TYPE: PRT
<213> ORGANISM: Homo sapiens

<400> SEQUENCE: 1

Met Leu Ser Arg Ala Val Cys Gly Thr Ser Arg Gln Leu Ala Pro Val
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Lys His His Ala Ala Tyr Val Asn Asn Leu Asn Val
    50                  55                  60

Thr Glu Glu Lys Tyr Gln Glu Ala Leu Ala Lys Gly Asp Val Thr Ala
65                  70                  75                  80

Gln Ile Ala Leu Gln Pro Ala Leu Lys Phe Asn Gly Gly Gly His Ile
                85                  90                  95

Asn His Ser Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
        115                 120                 125

Asp Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Lys
    210                 215                 220
```

-continued

```
<210> SEQ ID NO 2
<211> LENGTH: 222
<212> TYPE: PRT
<213> ORGANISM: Mus musculus

<400> SEQUENCE: 2

Met Leu Cys Arg Ala Ala Cys Ser Thr Gly Arg Arg Leu Gly Pro Val
 1               5                  10                  15

Ala Gly Ala Ala Gly Ser Arg His Lys His Ser Leu Pro Asp Leu Pro
             20                  25                  30

Tyr Asp Tyr Gly Ala Leu Glu Pro His Ile Asn Ala Gln Ile Met Gln
         35                  40                  45

Leu His His Ser Lys His His Ala Ala Tyr Val Asn Asn Leu Asn Ala
     50                  55                  60

Thr Glu Glu Lys Tyr His Glu Ala Leu Ala Lys Gly Asp Val Thr Thr
 65                  70                  75                  80

Gln Val Ala Leu Gln Pro Ala Leu Lys Phe Asn Gly Gly Gly His Ile
                 85                  90                  95

Asn His Thr Ile Phe Trp Thr Asn Leu Ser Pro Lys Gly Gly Gly Glu
            100                 105                 110

Pro Lys Gly Glu Leu Leu Glu Ala Ile Lys Arg Asp Phe Gly Ser Phe
        115                 120                 125

Glu Lys Phe Lys Glu Lys Leu Thr Ala Val Ser Val Gly Val Gln Gly
    130                 135                 140

Ser Gly Trp Gly Trp Leu Gly Phe Asn Lys Glu Gln Gly Arg Leu Gln
145                 150                 155                 160

Ile Ala Ala Cys Ser Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Thr Ala Cys Lys Lys
    210                 215                 220

<210> SEQ ID NO 3
<211> LENGTH: 217
<212> TYPE: PRT
<213> ORGANISM: Drosophila melanogaster

<400> SEQUENCE: 3

Met Phe Val Ala Arg Lys Ile Ser Gln Thr Ala Ser Leu Ala Val Arg
 1               5                  10                  15

Gly Lys His Thr Leu Pro Lys Leu Pro Tyr Asp Tyr Ala Ala Leu Glu
             20                  25                  30

Pro Ile Ile Cys Arg Glu Ile Met Glu Leu His His Gln Lys His His
         35                  40                  45

Gln Thr Tyr Val Asn Asn Leu Asn Ala Ala Glu Glu Gln Leu Glu Glu
     50                  55                  60

Ala Lys Ser Lys Ser Asp Thr Thr Lys Leu Ile Gln Leu Ala Pro Ala
 65                  70                  75                  80

Leu Arg Phe Asn Gly Gly Gly His Ile Asn His Thr Ile Phe Trp Gln
                 85                  90                  95

Asn Leu Ser Pro Asn Lys Thr Gln Pro Ser Asp Asp Leu Lys Lys Ala
            100                 105                 110

Ile Glu Ser Gln Trp Lys Ser Leu Glu Glu Phe Lys Lys Glu Leu Thr
```

```
                  115                 120                 125
Thr Leu Thr Val Ala Val Gln Gly Ser Gly Trp Gly Trp Leu Gly Phe
    130                 135                 140

Asn Lys Lys Ser Gly Lys Leu Gln Leu Ala Ala Leu Pro Asn Gln Asp
145                 150                 155                 160

Pro Leu Glu Ala Ser Thr Gly Leu Ile Pro Leu Phe Gly Ile Asp Val
                165                 170                 175

Trp Glu His Ala Tyr Tyr Leu Gln Tyr Lys Asn Val Arg Pro Ser Tyr
            180                 185                 190

Val Glu Ala Ile Trp Asp Ile Ala Asn Trp Asp Asp Ile Ser Cys Arg
        195                 200                 205

Phe Gln Glu Ala Lys Lys Leu Gly Cys
    210                 215

<210> SEQ ID NO 4
<211> LENGTH: 218
<212> TYPE: PRT
<213> ORGANISM: Schizosaccharomyces pombe

<400> SEQUENCE: 4

Met Leu Arg Phe Leu Ser Lys Asn Ser Val Ala Ala Ile Arg Asn Val
1               5                   10                  15

Ser Ile Ala Arg Gly Val His Thr Lys Ala Thr Leu Pro Pro Leu Pro
            20                  25                  30

Tyr Ala Tyr Asn Ala Leu Glu Pro Ala Leu Ser Glu Thr Ile Met Lys
        35                  40                  45

Leu His His Asp Lys His His Gln Thr Tyr Val Asn Asn Leu Asn Ala
    50                  55                  60

Ala Gln Glu Lys Leu Ala Asp Pro Asn Leu Asp Leu Glu Gly Glu Val
65                  70                  75                  80

Ala Leu Gln Ala Ala Ile Lys Phe Asn Gly Gly Gly His Ile Asn His
                85                  90                  95

Ser Leu Phe Trp Lys Ile Leu Ala Pro Gln Lys Glu Gly Gly Gly Lys
            100                 105                 110

Pro Val Thr Ser Gly Ser Leu His Lys Ala Ile Thr Ser Lys Trp Gly
        115                 120                 125

Ser Leu Glu Asp Phe Gln Lys Glu Met Asn Ala Ala Leu Ala Ser Ile
    130                 135                 140

Gln Gly Ser Gly Trp Ala Trp Leu Ile Val Asp Lys Asp Gly Ser Leu
145                 150                 155                 160

Arg Ile Thr Thr Thr Ala Asn Gln Asp Thr Ile Val Lys Ser Lys Pro
                165                 170                 175

Ile Ile Gly Ile Asp Ala Trp Glu His Ala Tyr Tyr Pro Gln Tyr Glu
            180                 185                 190

Asn Arg Lys Ala Glu Tyr Phe Lys Ala Ile Trp Asn Val Ile Asn Trp
        195                 200                 205

Lys Glu Ala Glu Ser Arg Tyr Ser Asn Arg
    210                 215

<210> SEQ ID NO 5
<211> LENGTH: 224
<212> TYPE: PRT
<213> ORGANISM: Xenopus laevis

<400> SEQUENCE: 5

Met Leu Cys Arg Leu Ser Val Cys Gly Arg Gly Arg Met Arg Cys Val
1               5                   10                  15
```

```
Pro Ala Leu Ala Tyr Ser Phe Cys Lys Glu Lys His Thr Leu Pro Asp
                20                  25                  30

Leu Pro Tyr Asp Tyr Gly Ala Leu Gln Pro His Ile Ser Ala Glu Ile
            35                  40                  45

Met Gln Leu His His Ser Lys His His Ala Thr Tyr Val Asn Asn Leu
 50                  55                  60

Asn Ile Thr Glu Glu Lys Tyr Ala Glu Ala Leu Ala Lys Gly Asp Val
 65                  70                  75                  80

Thr Thr Gln Val Ser Leu Gln Ala Ala Leu Lys Phe Asn Gly Gly Gly
                85                  90                  95

His Ile Asn His Thr Ile Phe Trp Thr Asn Leu Ser Pro Asn Gly Gly
                100                 105                 110

Gly Glu Pro Gln Gly Glu Leu Leu Asp Ala Ile Lys Arg Asp Phe Gly
            115                 120                 125

Ser Phe Glu Lys Phe Lys Glu Lys Leu Asn Thr Val Ser Val Gly Val
130                 135                 140

Gln Gly Ser Gly Trp Gly Trp Leu Gly Tyr Asn Lys Asp Ser Asn Arg
145                 150                 155                 160

Leu Gln Leu Ala Ala Cys Ala Asn Gln Asp Pro Leu Gln Gly Thr Thr
                165                 170                 175

Gly Leu Ile Pro Leu Leu Gly Ile Asp Val Trp Glu His Ala Tyr Tyr
            180                 185                 190

Leu Gln Tyr Lys Asn Val Arg Pro Asp Tyr Leu Lys Ala Ile Trp Asn
        195                 200                 205

Val Ile Asn Trp Glu Asn Val Thr Glu Arg Tyr Gln Ala Ser Lys Lys
210                 215                 220

<210> SEQ ID NO 6
<211> LENGTH: 233
<212> TYPE: PRT
<213> ORGANISM: Saccharomyces cerevisiae

<400> SEQUENCE: 6

Met Phe Ala Lys Thr Ala Ala Ala Asn Leu Thr Lys Lys Gly Gly Leu
 1               5                  10                  15

Ser Leu Leu Ser Thr Thr Ala Arg Arg Thr Lys Val Thr Leu Pro Asp
                20                  25                  30

Leu Lys Trp Asp Phe Gly Ala Leu Glu Pro Tyr Ile Ser Gly Gln Ile
            35                  40                  45

Asn Glu Leu His Tyr Thr Lys His His Gln Thr Tyr Val Asn Gly Phe
 50                  55                  60

Asn Thr Ala Val Asp Gln Phe Gln Glu Leu Ser Asp Leu Leu Ala Lys
 65                  70                  75                  80

Glu Pro Ser Pro Ala Asn Ala Arg Lys Met Ile Ala Ile Gln Gln Asn
                85                  90                  95

Ile Lys Phe His Gly Gly Gly Phe Thr Asn His Cys Leu Phe Trp Glu
            100                 105                 110

Asn Leu Ala Pro Glu Ser Gln Gly Gly Gly Glu Pro Pro Thr Gly Ala
        115                 120                 125

Leu Ala Lys Ala Ile Asp Glu Gln Phe Gly Ser Leu Asp Glu Leu Ile
130                 135                 140

Lys Leu Thr Asn Thr Lys Leu Ala Gly Val Gln Gly Ser Gly Trp Ala
145                 150                 155                 160

Phe Ile Val Lys Asn Leu Ser Asn Gly Gly Lys Leu Asp Val Val Gln
                165                 170                 175
```

-continued

Thr Tyr Asn Gln Asp Thr Val Thr Gly Pro Leu Val Pro Leu Val Ala
            180                 185                 190

Ile Asp Ala Trp Glu His Ala Tyr Tyr Leu Gln Tyr Gln Asn Lys Lys
        195                 200                 205

Ala Asp Tyr Phe Lys Ala Ile Trp Asn Val Val Asn Trp Lys Glu Ala
    210                 215                 220

Ser Arg Arg Phe Asp Ala Gly Lys Ile
225                 230

<210> SEQ ID NO 7
<211> LENGTH: 222
<212> TYPE: PRT
<213> ORGANISM: Rattus norvegicus

<400> SEQUENCE: 7

Met Leu Cys Arg Ala Ala Cys Ser Ala Gly Arg Arg Leu Gly Pro Ala
1               5                   10                  15

Ala Ser Thr Ala Gly Ser Arg His Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Lys His His Ala Thr Tyr Val Asn Asn Leu Asn Val
    50                  55                  60

Thr Glu Glu Lys Tyr His Glu Ala Leu Ala Lys Gly Asp Val Thr Thr
65                  70                  75                  80

Gln Val Ala Leu Gln Pro Ala Leu Lys Phe Asn Gly Gly Gly His Ile
                85                  90                  95

Asn His Ser Ile Phe Trp Thr Asn Leu Ser Pro Lys Gly Gly Gly Glu
            100                 105                 110

Pro Lys Gly Glu Leu Leu Glu Ala Ile Lys Arg Asp Phe Gly Ser Phe
        115                 120                 125

Glu Lys Phe Lys Glu Lys Leu Thr Ala Val Ser Val Gly Val Gln Gly
    130                 135                 140

Ser Gly Trp Gly Trp Leu Gly Phe Asn Lys Glu Gln Gly Arg Leu Gln
145                 150                 155                 160

Ile Ala Ala Cys Ser Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Ser Gln Arg Tyr Ile Val Cys Lys Lys
    210                 215                 220

<210> SEQ ID NO 8
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 8

Met Leu Ser Arg Ala Val Cys Gly Thr Ser Arg Gln Leu Ala Pro Val
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln

```
                    35                  40                  45
Leu His His Ser Arg His His Ala Ala Tyr Val Asn Asn Leu Asn Val
    50                  55                  60

Thr Glu Glu Lys Tyr Gln Glu Ala Leu Ala Lys Gly Asp Val Thr Ala
65                  70                  75                  80

Gln Ile Ala Leu Gln Pro Ala Leu Arg Phe Asn Gly Gly His Ile
                    85                  90                  95

Asn His Ser Ile Phe Trp Thr Asn Leu Ser Pro Asn Gly Gly Gly Glu
                100                 105                 110

Pro Lys Gly Glu Leu Leu Glu Ala Ile Lys Arg Asp Phe Gly Ser Phe
                115                 120                 125

Asp Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
                180                 185                 190

Tyr Lys Asn Val Arg Pro Asp Tyr Leu Lys Ala Ile Trp Asn Val Ile
                195                 200                 205

Asn Trp Glu Asn Val Thr Glu Arg Tyr Met Ala Cys Lys Lys
    210                 215                 220

<210> SEQ ID NO 9
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 9

Met Leu Ser Arg Ala Val Cys Gly Thr Ser Arg Gln Leu Ala Pro Val
1               5                   10                  15

Leu Gly Tyr Leu Gly Ser Arg Gln Lys His Ser Leu Pro Asp Leu Pro
                20                  25                  30

Tyr Asp Tyr Gly Ala Leu Glu Pro His Ile Asn Ala Gln Ile Met Gln
                35                  40                  45

Leu His His Ser Arg His His Ala Ala Tyr Val Asn Asn Leu Asn Ala
    50                  55                  60

Thr Glu Glu Lys Tyr Gln Glu Ala Leu Ala Lys Gly Asp Val Thr Ala
65                  70                  75                  80

Gln Ile Ala Leu Gln Pro Ala Leu Arg Phe Asn Gly Gly Gly His Ile
                85                  90                  95

Asn His Ser Ile Phe Trp Thr Asn Leu Ser Pro Asn Gly Gly Gly Glu
                100                 105                 110

Pro Lys Gly Glu Leu Leu Glu Ala Ile Lys Arg Asp Phe Gly Ser Phe
                115                 120                 125

Asp Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
                180                 185                 190
```

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Lys
210                 215                 220

<210> SEQ ID NO 10
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 10

Met Leu Ser Arg Ala Val Cys Gly Thr Ser Arg Gln Leu Ala Pro Val
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Arg His His Ala Ala Tyr Val Asn Asn Leu Asn Val
50                  55                  60

Thr Glu Glu Lys Tyr Gln Glu Ala Leu Ala Lys Gly Asp Val Thr Thr
65                  70                  75                  80

Gln Ile Ala Leu Gln Pro Ala Leu Arg Phe Asn Gly Gly Gly His Ile
                85                  90                  95

Asn His Ser Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
        115                 120                 125

Asp Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Lys
210                 215                 220

<210> SEQ ID NO 11
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 11

Met Leu Ser Arg Ala Val Cys Gly Thr Ser Arg Gln Leu Ala Pro Val
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Arg His His Ala Ala Tyr Val Asn Asn Leu Asn Val
50                  55                  60

```
Thr Glu Glu Lys Tyr Gln Glu Ala Leu Ala Lys Gly Asp Val Thr Ala
 65                  70                  75                  80

Gln Val Ala Leu Gln Pro Ala Leu Arg Phe Asn Gly Gly His Ile
             85                  90                  95

Asn His Ser Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
            115                 120                 125

Asp Lys Phe Lys Glu Lys Leu Thr Ala Ala Ser Val Gly Val Gln Gly
            130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
            165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
            195                 200                 205

Asn Trp Glu Asn Val Thr Glu Arg Tyr Met Ala Cys Lys Lys
            210                 215                 220

<210> SEQ ID NO 12
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 12

Met Leu Ser Arg Ala Val Cys Gly Thr Ser Arg Gln Leu Ala Pro Val
  1               5                  10                  15

Leu Gly Tyr Leu Gly Ser Arg Gln Lys His Ser Leu Pro Asp Leu Pro
             20                  25                  30

Tyr Asp Tyr Gly Ala Leu Glu Pro His Ile Asn Ala Gln Ile Met Gln
         35                  40                  45

Leu His His Ser Arg His His Ala Ala Tyr Val Asn Asn Leu Asn Val
 50                  55                  60

Thr Glu Glu Lys Tyr Gln Glu Ala Leu Ala Lys Gly Asp Val Thr Ala
 65                  70                  75                  80

Gln Ile Ala Leu Gln Pro Ala Leu Arg Phe Asn Gly Gly Gly His Ile
             85                  90                  95

Asn His Thr Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
            115                 120                 125

Asp Lys Phe Lys Glu Lys Leu Thr Ala Ala Ser Val Gly Val Gln Gly
            130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
            165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
            195                 200                 205
```

```
Asn Trp Glu Asn Val Thr Glu Arg Tyr Met Ala Cys Lys Lys
210                 215                 220
```

<210> SEQ ID NO 13
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 13

```
Met Leu Ser Arg Ala Val Cys Gly Thr Ser Arg Gln Leu Ala Pro Val
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Arg His His Ala Ala Tyr Val Asn Asn Leu Asn Val
    50                  55                  60

Thr Glu Glu Lys Tyr Gln Glu Ala Leu Ala Lys Gly Asp Val Thr Ala
65                  70                  75                  80

Gln Ile Ala Leu Gln Pro Ala Leu Arg Phe Asn Gly Gly Gly His Ile
                85                  90                  95

Asn His Ser Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
        115                 120                 125

Glu Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Lys
    210                 215                 220
```

<210> SEQ ID NO 14
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 14

```
Met Leu Ser Arg Ala Val Cys Gly Thr Ser Arg Gln Leu Ala Pro Val
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Arg His His Ala Ala Tyr Val Asn Asn Leu Asn Val
    50                  55                  60

Thr Glu Glu Lys Tyr Gln Glu Ala Leu Ala Lys Gly Asp Val Thr Ala
65                  70                  75                  80
```

Gln Ile Ala Leu Gln Pro Ala Leu Arg Phe Asn Gly Gly His Ile
                85                  90                  95

Asn His Ser Ile Phe Trp Thr Asn Leu Ser Pro Asn Gly Gly Glu
                100                 105                 110

Pro Lys Gly Glu Leu Leu Glu Ala Ile Lys Arg Asp Phe Gly Ser Phe
            115                 120                 125

Asp Lys Phe Lys Glu Lys Leu Thr Ala Val Ser Val Gly Val Gln Gly
        130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
                180                 185                 190

Tyr Lys Asn Val Arg Pro Asp Tyr Leu Lys Ala Ile Trp Asn Val Ile
            195                 200                 205

Asn Trp Glu Asn Val Thr Glu Arg Tyr Met Ala Cys Lys Lys
        210                 215                 220

<210> SEQ ID NO 15
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 15

Met Leu Ser Arg Ala Val Cys Gly Thr Ser Arg Gln Leu Ala Pro Val
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Arg His His Ala Ala Tyr Val Asn Asn Leu Asn Val
50              55                  60

Thr Glu Glu Lys Tyr Gln Glu Ala Leu Ala Lys Gly Asp Val Thr Ala
65                  70                  75                  80

Gln Ile Ala Leu Gln Pro Ala Leu Arg Phe Asn Gly Gly His Ile
                85                  90                  95

Asn His Ser Ile Phe Trp Thr Asn Leu Ser Pro Asn Gly Gly Glu
                100                 105                 110

Pro Lys Gly Glu Leu Leu Glu Ala Ile Lys Arg Asp Phe Gly Ser Phe
            115                 120                 125

Asp Lys Phe Lys Glu Lys Leu Thr Ala Ala Ser Val Gly Val Gln Gly
        130                 135                 140

Ser Gly Trp Gly Trp Leu Gly Phe Asn Lys Glu Gln Gly Arg Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
                180                 185                 190

Tyr Lys Asn Val Arg Pro Asp Tyr Leu Lys Ala Ile Trp Asn Val Ile
            195                 200                 205

Asn Trp Glu Asn Val Thr Glu Arg Tyr Met Ala Cys Lys Lys
        210                 215                 220

```
<210> SEQ ID NO 16
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 16

Tyr Gly Arg Lys Lys Arg Arg Gln Arg Arg Arg
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 17

Arg Arg Gln Arg Arg Thr Ser Lys Leu Met Lys Arg
1               5                   10

<210> SEQ ID NO 18
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 18

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 19
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 19

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 20
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 20

Arg Gln Ile Lys Ile Trp Phe Gln Asn Arg Arg Met Lys Trp Lys Lys
1               5                   10                  15

<210> SEQ ID NO 21
<211> LENGTH: 9
<212> TYPE: PRT
<213> ORGANISM: Artificial Sequence
<220> FEATURE:
<223> OTHER INFORMATION: Synthetic polypeptide
```

```
<400> SEQUENCE: 21

Arg Lys Lys Arg Arg Gln Arg Arg Arg
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 22

Tyr Ala Arg Ala Ala Ala Arg Gln Ala Arg Ala
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 23

Thr His Arg Leu Pro Arg Arg Arg Arg Arg
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 24

Gly Gly Arg Arg Ala Arg Arg Arg Arg Arg
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 25

Cys Tyr Pro Tyr Asp Val Pro Asp Tyr Ala
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 26

Asp Tyr Lys Asp Asp Asp Asp Lys
1               5

<210> SEQ ID NO 27
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 27
```

Cys Glu Gln Lys Leu Ile Ser Glu Glu Asp Leu
1               5                   10

<210> SEQ ID NO 28
<211> LENGTH: 405
<212> TYPE: PRT
<213> ORGANISM: Homo sapiens

<400> SEQUENCE: 28

Met Ala Phe Trp Gly Trp Arg Ala Ala Ala Leu Arg Leu Trp Gly
1               5                   10                  15

Arg Val Val Glu Arg Val Glu Ala Gly Gly Val Gly Pro Phe Gln
                20                  25                  30

Ala Cys Gly Cys Arg Leu Val Leu Gly Gly Arg Asp Asp Val Ser Ala
                35                  40                  45

Gly Leu Arg Gly Ser His Gly Ala Arg Gly Glu Pro Leu Asp Pro Ala
        50                  55                  60

Arg Pro Leu Gln Arg Pro Pro Arg Pro Glu Val Pro Arg Ala Phe Arg
65                  70                  75                  80

Arg Gln Pro Arg Ala Ala Ala Pro Ser Phe Phe Ser Ser Ile Lys
                85                  90                  95

Gly Gly Arg Arg Ser Ile Ser Phe Ser Val Gly Ala Ser Ser Val Val
                100                 105                 110

Gly Ser Gly Gly Ser Ser Asp Lys Gly Lys Leu Ser Leu Gln Asp Val
            115                 120                 125

Ala Glu Leu Ile Arg Ala Arg Ala Cys Gln Arg Val Val Val Met Val
        130                 135                 140

Gly Ala Gly Ile Ser Thr Pro Ser Gly Ile Pro Asp Phe Arg Ser Pro
145                 150                 155                 160

Gly Ser Gly Leu Tyr Ser Asn Leu Gln Gln Tyr Asp Leu Pro Tyr Pro
                165                 170                 175

Glu Ala Ile Phe Glu Leu Pro Phe Phe Phe His Asn Pro Lys Pro Phe
                180                 185                 190

Phe Thr Leu Ala Lys Glu Leu Tyr Pro Gly Asn Tyr Lys Pro Asn Val
            195                 200                 205

Thr His Tyr Phe Leu Arg Leu Leu His Asp Lys Gly Leu Leu Leu Arg
        210                 215                 220

Leu Tyr Thr Gln Asn Ile Asp Gly Leu Glu Arg Val Ser Gly Ile Pro
225                 230                 235                 240

Ala Ser Lys Leu Val Glu Ala His Gly Thr Phe Ala Ser Ala Thr Cys
                245                 250                 255

Thr Val Cys Gln Arg Pro Phe Pro Gly Glu Asp Ile Arg Ala Asp Val
                260                 265                 270

Met Ala Asp Arg Val Pro Arg Cys Pro Val Cys Thr Gly Val Val Lys
            275                 280                 285

Pro Asp Ile Val Phe Phe Gly Glu Pro Leu Pro Gln Arg Phe Leu Leu
        290                 295                 300

His Val Asp Phe Pro Met Ala Asp Leu Leu Leu Ile Leu Gly Thr
305                 310                 315                 320

Ser Leu Glu Val Glu Pro Phe Ala Ser Leu Thr Glu Ala Val Arg Ser
                325                 330                 335

Ser Val Pro Arg Leu Leu Ile Asn Arg Asp Leu Val Gly Pro Leu Ala
            340                 345                 350

Trp His Pro Arg Ser Arg Asp Val Ala Gln Leu Gly Asp Val Val His
        355                 360                 365

```
Gly Val Glu Ser Leu Val Glu Leu Leu Gly Trp Thr Glu Glu Met Arg
            370                 375                 380

Asp Leu Val Gln Arg Glu Thr Gly Lys Leu Asp Gly Pro Asp Lys Ser
385                 390                 395                 400

Glu Gln Ile Asp Asn
                405

<210> SEQ ID NO 29
<211> LENGTH: 1200
<212> TYPE: DNA
<213> ORGANISM: Homo sapiens

<400> SEQUENCE: 29
atggcgttct ggggttggcg cgccgcggca gccctccggc tgtggggccg ggtagttgaa      60
cgggtcgagg ccggggagg cgtggggccg tttcaggcct gcggctgtcg gctggtgctt     120
ggcggcaggg acgatgtgag tgcggggctg agaggcagcc atgggccccg cggtgagccc     180
ttggacccgg cgcgcccctt gcagaggcct cccagacccg aggtgcccag gcattccgg      240 aggcagccga ggcagcagc tcccagtttc ttcttttcga gtattaaagg tggaagaagg      300
tccatatctt tttctgtggg tgcttcaagt gttgttggaa gtggaggcag cagtgacaag     360
gggaagcttt ccctgcagga tgtagctgag ctgattcggg ccagagcctg ccagagggtg     420
gtggtcatgg tggggccgg catcagcaca cccagtggca ttccagactt cagatcgccg     480
gggagtggcc tgtacagcaa cctccagcag tacgatctcc cgtaccccga ggccattttt     540
gaactcccat tcttctttca aaccccaag ccctttttca ctttggccaa ggagctgtac     600
cctggaaact acaagcccaa cgtcactcac tactttctcc ggctgcttca tgacaagggg     660
ctgcttctgc ggctctacac gcagaacatc gatgggcttg agagtgtc gggcatccct     720 gcctcaaagc tggttgaagc tcatggaacc tttgcctctg ccacctgcac agtctgccaa     780
agacccttcc caggggagga cattcggggct gacgtgatgg cagacagggt tccccgctgc     840
ccggtctgca ccggcgttgt gaagcccgac attgtgttct ttggggagcc gctgcccag      900 aggttcttgc tgcatgtggt tgatttcccc atggcagatc tgctgctcat ccttgggacc     960
tccctggagg tggagccttt tgccagcttg accgaggccg tgcggagctc agttccccga    1020
ctgctcatca accgggactt ggtggggccc ttggcttggc atcctcgcag cagggacgtg    1080
gcccagctgg gggacgtggt tcacggcgtg gaaagcctag tggagcttct gggctggaca    1140
gaagagatgc gggaccttgt gcagcgggaa actgggaagc ttgatggacc agacaaatag    1200

<210> SEQ ID NO 30
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 30

Gln Ile Met Gln Leu His His Ser Lys His His
  1               5                  10

<210> SEQ ID NO 31
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 31
```

```
Gln Ile Met Gln Leu His His Ser Lys His His
 1               5                  10
```

```
<210> SEQ ID NO 32
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 32

Glu Ile Met Thr Leu His His Lys Lys His His
 1               5                  10
```

```
<210> SEQ ID NO 33
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 33

Thr Ile Met Lys Leu His His Asp Lys His His
 1               5                  10
```

```
<210> SEQ ID NO 34
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 34

Gln Ile Asn Glu Leu His Tyr Thr Lys His His
 1               5                  10
```

```
<210> SEQ ID NO 35
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 35

Glu Thr Met Glu Ile His His Asp Arg His His
 1               5                  10
```

```
<210> SEQ ID NO 36
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 36

Gln Thr Met Glu Ile His His Thr Lys His His
 1               5                  10
```

```
<210> SEQ ID NO 37
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 37

Gln Pro Ala Leu Lys Phe Asn Gly Gly Gly His Ile Asn His Ser Ile
 1               5                  10                  15
```

Phe

```
<210> SEQ ID NO 38
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 38
```

Gln Pro Ala Leu Lys Phe Asn Gly Gly Gly His Ile Asn His Thr Ile
1               5                   10                  15

Phe

```
<210> SEQ ID NO 39
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 39
```

Gln Ser Ala Ile Lys Phe Asn Gly Gly Gly His Val Asn His Ser Ile
1               5                   10                  15

Phe

```
<210> SEQ ID NO 40
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 40
```

Gln Ala Ala Ile Lys Phe Asn Gly Gly Gly His Ile Asn His Ser Leu
1               5                   10                  15

Phe

```
<210> SEQ ID NO 41
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 41
```

Gln Gln Asn Ile Lys Phe His Gly Gly Gly Phe Thr Asn His Cys Leu
1               5                   10                  15

Phe

```
<210> SEQ ID NO 42
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 42
```

Gln Thr Ala Val Arg Asn Asn Gly Gly Gly His Leu Asn His Ser Leu
1               5                   10                  15

Phe

```
<210> SEQ ID NO 43
```

```
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 43

Lys Thr Val Leu Arg Asn Asn Ala Gly Gly His Ala Asn His Ser Leu
 1               5                  10                  15

Phe
```